US006781031B2

(12) United States Patent
Langham

(10) Patent No.: US 6,781,031 B2
(45) Date of Patent: Aug. 24, 2004

(54) NON-DEHISCENT SESAME VARIETY S26

(75) Inventor: Derald Ray Langham, San Antonio, TX (US)

(73) Assignee: Sesaco Corporation, Paris (FR)

( * ) Notice: Subject to any disclaimer, the term of this patent is extended or adjusted under 35 U.S.C. 154(b) by 0 days.

(21) Appl. No.: 10/189,800

(22) Filed: Jul. 3, 2002

(65) Prior Publication Data

US 2004/0016031 A1 Jan. 22, 2004

(51) Int. Cl.$^7$ .............................. A01H 1/00; A01H 5/00; A01H 5/10
(52) U.S. Cl. ....................... 800/260; 800/298; 800/295; 435/430; 435/430.1
(58) Field of Search ................................ 800/260, 298, 800/295, 268; 435/430, 430.1

(56) References Cited

U.S. PATENT DOCUMENTS 6,100,452 A   8/2000   Langham ..................... 800/298

FOREIGN PATENT DOCUMENTS

WO   9915681   4/1999   ............ C12N/15/82
WO   0013488   3/2000   ............ A01H/5/00

OTHER PUBLICATIONS

Ashri, A. 1998. "Sesame Breeding," *Plant Breeding Reviews* 16:179–228.
Ashri, A. 1989. "Sesame," Chapter 18, *Oil Crops of the World*, McGraw–Hill Publishing Co., New York; pp. 375–387.
Bakheit, et al. 1996. "Inheritance of some qualitative and quantitative characters in sesame, Sesamum indicum L.," *Assiut Journal of the Agricultural Sciences* 27:27–41.
Day, Jamie. 1998. "The mechanism of indehiscence in sesame. Features that might be useful in a breeding programme," Third FAO/IAEA Research Coordination Meeting on Induced Mutations for Sesame Improvements Bangkok, Thailand, Apr. 6–10, 1998; 11 pages.
Delgado, et al. 1992. "Analisis Del Cruzamiento Dialelico De Seis Variedades Indehiscentes Y Dos Dehiscentes Ajonjoli Sesamum indicum L.$^1$," *Agronomia Tropical* 42:191–210.
Hutson, B. D. 1983. "Standards for the inspection and grading of sesame seed," Hutson Laboratories, Yuma, Arizona, pp. 1–5.
IBPGR Secretariat. 1981. "Descriptors for Sesame" *International Board For Plant Genetic Resources*, Rome, pp. 1–19.

Kalton, R.R. 1949. "Sesame, a promising new oilseed crop for Texas," *Proceeding of 1$^{st}$ International Sesame Conference*, Clemson, South Carolina; pp 62–65.
Langham, D.G. 1944. "Natural and controlled pollination in sesame," *Journal of Heredity* 8:254–256.
Langham, D.G. and Rodriguez, M. 1949. "Improvement in Sesame in Venezuela," *Proceedings of 1$^{st}$ International Sesame Conference*, Clemson, South Carolina; pp74–79.
Langham, et al. 1956. "Dehiscencia y otras caracteristicas del ajonjoli, Sesamum indicum L., en relacion con el problema de la cosecha," *Genesa*, Maracay, Venezuela; pp. 3–16.
Langham, D.R. 1998. "Shatter resistance in Sesame," Third FAO/IAEA Research Coordination Meeting on Induced Mutations for Sesame Improvements, Bangkok, Thailand, Apr. 6–10, 1998; 14 pages.
Langham, D. R. and Wiemers, T. 2002. "Progress in mechanizing sesame in the US through breeding," *Trends in New Crops and New Uses*, J. Janick and A. Whipkey (eds), ASHS Press, Alexandria, Virginia; pp. 157–173.
Narniki, Mitsuo. 1995. "The Chemistry and Physiological Functions and Sesame" *Food Reviews International* 11: 281–329.
Osman, H.E. 1985. "Studies in sesame: hybridization and related techniques," *FAO Plant Production and Protection Paper* No. 66, pp. 145–156.
"Recommendations for the Discussion Groups," 1995. *Proceeding of Sesame Workshop*, Darwin and Katherine, Northern Territory, Australia, Mar. 21–23, 1995, pp. 252–257.
Shiego, et al. 1994. "Breeding of good quality sesame with dehiscence resistance and strong antioxidative property," *Baiorunessansu keikaku* (abstact only).
Weiss, E. A. 1971. "History," *Castor, Sesame and Safflower*, Leonard–Hill Books, London; pp 311–525.
Weiss, E.A. 1983. "Sesame," *Oilseed Crops*, Longman Inc. New York, pp. 282–340.
Weiss. 2000. "Sesame" *Oilseed Crops*, Longman Inc. New York; pp. 131–164.
Yermanos, D.M. 1980. "Sesame," *Hybridization of Crop plants*, American Society of Agronomy–Crop Science Society of American, Madison, Wisconsin; pp. 549–563.
Zanten, L. van (ed). 1996. "Conclusions and Reccomendations," 2$^{nd}$ FAO/IAEA Research Coordination Meeting, Antalya, Turkey. pp. 107–113.

*Primary Examiner*—Ashwin Mehta
*Assistant Examiner*—Medina A. Ibrahim
(74) *Attorney, Agent, or Firm*—Sidley Austin Brown & Wood LLP

(57) ABSTRACT

A non-dehiscent sesame (*Sesamum indicum* L.) designated S26 has been found. Its degree of shatter resistance, or seed retention, makes S26 suitable for mechanized harvesting.

10 Claims, 6 Drawing Sheets

```
                                        /111   (1)
                                   /111X  (2)
                              |         \BEE
                        /F820 (3)
                        |     \104  (4)
                   /578 (5)
                   |    |     /104  (4)
                   |    \F853 (6)
                   |          \192  (7)
              /031 (8)
              |    \118  (9)
       /BI954 (10)
       |      |         /72C  (11)
       |      |    /L6651 (12)
       |      |    |    |    /G8   (13)
       |      |    |    |    \804  (14)
       |      |    |    |         /111  (1)
       |      |    |    |         \111X (2)
       |      |    |    |              \BEE
       |      \2CA (15)
       |           |   /G8  (13)
       |           \S11 (16)
       |                |    /111  (1)
       |                \111X (2)
       |                      \BEE
    S26 (38)
       |                            /SOMALIA (17)
       |                     /H6778 (18)
       |                     |      \118  (9)
       |                /J3208 (19)
       |                |    |       /193  (20)
       |                |    \H6432 (21)
       |                |          |     /MAX  (22)
       |                |          \076  (23)
       |                |                |       /R234 (24)
       |                |                \R234 TALL (25)
       |                |                       \BEE
       |       /K3255 (26)
       |       |    |                /G8  (13)
       |       |    |          /045 (27)
       |       |    |          |    \G958-1 (28)
       |       |    |    /H6785 (29)
       |       |    |    |    |     /982  (30)
       |       |    |    |    \036  (31)
       |       |    |    |           \G53.80-1 (32)
       |       |    \J3222 (33)
       |       |         |            /192  (7)
       |       |         |      /195 (34)
       |       |         |      |    \BEE
       |       |         \H6562 (35)
       |       |                \701  (36)
       \S16 (37)
          |   /G8  (13)
          \S11 (16)
              |    /111  (1)
              \111X (2)
                   \BEE
```

Fig. 1

NON-DEHISCENT SESAME VARIETY S26

BACKGROUND

Sesame, or *Sesamum indicum*, is a tropical annual cultivated worldwide for its oil and its nut flavored seeds. In the Middle East, sesame is consumed as tahini, a sesame butter or sesame paste which is often mixed with ground chickpea kernels in a food preparation called hummus. Sesame is used widely in China, Japan, and Korea as a cooking oil, and it is consumed for its medicinal qualities. In recent years, the Japanese have been identifying and quantifying the medicinal benefits of sesame. In vitro studies and animal studies have indicated several antioxidant properties of sesame (Namiki, M. 1995. "The chemistry and physiological functions of sesame," *Food Rev Int* 11:281-329). In the western hemisphere, sesame is primarily used in the confectionary trade in rolls and crackers. Throughout the world, sesame seeds or paste are mixed into sweets, e.g., halva. Sesame oil use in the cosmetic industry continues to expand.

The sesame plant grows to a height of about 56–249 cm, and at its leaf axils are found capsules which contain the sesame seed. Upon maturity in nature, the capsules holding the sesame seeds begin to dry down, the capsules normally split open, and the seeds fall out. Commercially, the harvester tries to recover as much seed as possible from mature capsules. From ancient times through the present, the opening of the capsule has been the major factor in attempting to successfully collect the seed. Harvesting methods, weather, and plant characteristics all contribute to the amount of seed recovered.

The majority of the world's sesame is harvested manually. With manual non-mechanized methods, it is desirable for the sesame seed to fall readily from the plant. Upon physiological maturity, the sesame stalks are cut, tied into small bundles, and then stacked in shocks. Further harvesting procedures vary from country to country and from area to area within countries. Some move the shocks to a threshing floor so that the seed that falls out can be recovered. Others put plastic or cloth in the fields under the shocks to catch the seed. For manual harvesting methods in which the dried, shocked sesame is moved to a threshing floor or over a plastic or cloth, preferred plant varieties include dehiscent, or super shattering, in which less than 10% of the seeds set are retained in the capsule.

Other methods involve leaving the shocks in the fields, and when the shocks are dry, the sesame is turned upside down and struck with an implement to shake out all of the seed. For this type of manual harvesting method, it is preferred that the capsule hold as much of the sesame seed as possible until the farmer inverts the stalk. Plant varieties rated as shattering which retain as much seed as possible before inversion are preferred. Common methods of manual harvest are discussed in Weiss, E. A. "Sesame", *Oilseed crops* ($2^{nd}$ ed.), Chapter 5, Blackwell Science, Inc., Malden, Mass., p.131–164 (2000).

In an effort to mechanize the harvest of sesame, D. G. Langham introduced the use of swathers in Venezuela in 1944. The swathers were used to cut the sesame plants, manual labor was used to bundle and shock the cut plants, and combines were brought in to thrash the shocks. It was determined that seed shattering during mechanized harvesting methods caused considerable loss of sesame seed. While mechanization was considered to be essential for crop production in the Western hemisphere, it became obvious that the dehiscence of the sesame seed pod was the principal obstacle to the widespread acceptance of sesame as a commercial crop. (Langham, D. G. 1949. "Improvement of Sesame in Venezuela," *Proceedings First International Sesame Conference,* Clemson Agricultural College, Clemson, S.C., pp. 74–79). As programs to introduce sesame production in the United States in Arizona, South Carolina, Nebraska, Oklahoma, and Texas were initiated, mechanization was considered essential due to high labor costs. Kalton, one of the Texas researchers, reported that the shattering nature of available strains was the main obstacle in complete mechanization of the sesame crop. (Kalton, R. 1949. "Sesame, a promising new oilseed crop for Texas," *Proc First International Sesame Conference,* Clemson Agricultural College, Clemson, S.C., pp. 62–66).

In 1943, D. G. Langham found a mutation on a sesame plant. Capsules did not open on plants expressing this mutation. In succeeding generations, Langham showed that it was a recessive single gene which produced this indehiscence, where all the seeds were retained inside the unopened capsule. While it was believed that indehiscence would solve the problem of seed loss on mechanized harvesting, it was found that the capsules were too tough to effectively release the seed. Many of the capsules passed through a combine without opening. When more rigorous combining was attempted, an increase in efficiency of capsule opening was achieved but at the expense of seed quality. Seeds were broken due to the more rigorous combine conditions, and the broken seeds released free fatty acids. Chemical reactions with free fatty acids led to rancidity and concomitant undesirability of the harvested seed.

The indehiscent sesame varieties described above were used by various plant breeders in an attempt to develop desirable sesame lines. In addition to traditional crossbreeding approaches, some attempted to alter the chromosome numbers through tetraploids and interspecific crosses. Yermanos attempted to improve release of seed by increasing the length of the capsule so that there would be more surface for the combine to crack the capsules open (personal communication). Unfortunately, even with a small opening on the top of the capsule, a high percentage of broken seed was found on mechanized harvesting, preventing commercial use of this sesame line.

D. G. Langham reported in the late 1950's that the placenta attachment between each sesame seed and the placenta was important in the retention of seed in the capsule. He believed that he could improve the shatter resistance of sesame with increased placenta attachment but did not believe that all the seed could be retained in the capsule (Langham, D. G., Rodriguez, Maximo, and Reveron Esteban. 1956. "Dehiscencia y otras caracteristicas del ajonjoli, *Sesamum indicum* L., en relación con el problema de la cosecha", Genesa, Maracay, Venezuela, pp. 3–16). However, Yermanos reported that during capsule maturity, the placenta attachment gradually weakens and is obliterated when the capsule is completely desiccated. (Yermanos, D. M. 1980. "Sesame. Hybridization of crop plants," *Am Soc Agronomy-Crop Sci of America,* pp. 549–563). Thus, it appeared that the placenta attachment would have little effect on seed retention in dry, mature capsules during harvesting. A seamless gene which retained all the seed in the capsules was discovered by D. G. Langham and D. R. Langham in 1986. This was crossed with shattering types, and some progeny had an opening at the tip of the capsule. The seamless capsules were similar to the indehiscent capsules in that it was too difficult to remove the seed from the capsule without damaging the seed.

In 1982, the first non-shattering line (retaining 50–70% of the seeds set) requiring no manual labor was introduced.

This line could be harvested by swathing the sesame, leaving it to dry in the field, and then picking it up by a combine. Although complete mechanization was achieved, extensive loss of seed due to adverse weather conditions continued to occur. (Langham, D. R., "Shatter resistance in sesame", In: L. Van Zanten (ed.), Sesame improvements by induced mutations, *Proc. Final FAO/IAEA Co-ord. Res. Mtng.*, IAEA, Vienna, TECDOC-1195, p.51–61 (2001)).

Other varieties were developed between 1988 and 1997 which allowed for direct combining with 70–90% seed retention, but extensive loss of seed due to wind and rain continued to occur. Lines that generally yielded 80% of the seed under ideal conditions would yield only 45–65% under adverse conditions. Thus, while many of the crosses began to moderate the deleterious effects of mechanized harvesting, none were able to increase the yields to the level of manually harvesting shattering cultivars.

U.S. Pat. No. 6,100,452 which issued Aug. 8, 2000, disclosed non-dehiscent sesame lines Sesaco 22 (S22), Sesaco 23 (S23), Sesaco 24 (S24), 19A, and 11W, representative seed having been deposited under ATCC accession number PTA-1400, PTA-1401, PTA-1402, PTA-1399, and PTA-1398, respectively. These sesame lines are characterized by their high degree of seed retention within the capsule despite adverse weather conditions such as wind and rain and the retention of a sufficient amount of sesame seed during mechanized harvesting to be competitive with manual harvesting with minimization of seed breakage.

U.S. patent application Ser. No. 10/135,855, filed Apr. 30, 2002, disclosed a non-dehiscent sesame cultivar S25, representative seed having been deposited under ATCC accession number PTA-4258. S25 is a stable, commercially suitable sesame line providing an early maturity cycle which extends the planting region to more northern latitudes and improved resistance against common fungal diseases.

A non-dehiscent variety designated S26 has now been found which provides some improvements over previously disclosed non-dehiscent sesame lines.

SUMMARY OF THE INVENTION

In one aspect, the present invention is seed of a sesame plant S26, a sample of the seed having been deposited under ATCC Patent Deposit Designation No. PTA-4317.

In another aspect, the present invention is a sesame plant or its parts produced by growing the seed of sesame plant S26, a sample of the seed having been deposited under ATCC Patent Deposit Designation No. PTA-4317. Pollen is one of the sesame plant parts of the present invention.

In another aspect, the present invention is a sesame plant having all the physiological and morphological characteristics of sesame plant S26, a sample of the seed of sesame plant S26 having been deposited under ATCC Patent Deposit Designation No. PTA-4317.

In another aspect, the present invention is a sesame plant having all the physiological and morphological characteristics of a sesame plant produced by growing the seed having been deposited under ATCC Patent Deposit Designation No. PTA-4317.

In another aspect, the present invention is a sesame plant or its parts having as a parent sesame plant S26, a sample of the seed of sesame plant S26 having been deposited under ATCC Patent Deposit Designation No. PTA-4317.

In another aspect, the present invention is seed from a progeny sesame plant having as a parent sesame plant S26, a sample of the seed of sesame plant S26 having been deposited under ATCC Patent Deposit Designation No. PTA-4317.

In another aspect, the present invention is seed from a progeny sesame plant having as a parent a sesame plant produced by the seed having been deposited under ATCC Patent Deposit Designation No. PTA-4317.

In another aspect, the present invention is a tissue culture of seed having been deposited under ATCC Patent Deposit Designation No. PTA-4317.

In another aspect, the present invention is a tissue culture of sesame plant S26 or its parts, a sample of the seed of sesame plant S26 having been deposited under ATCC Patent Deposit Designation No. PTA-4317.

In another aspect, the present invention is a sesame plant regenerated from a tissue culture of a seed having been deposited under ATCC Patent Deposit Designation No. PTA-4317, wherein the regenerated sesame plant has all the physiological and morphological characteristics of a sesame plant produced by the seed deposited under ATCC Patent Deposit Designation No. PTA-4317.

In another aspect, the present invention is a sesame plant regenerated from a tissue culture of sesame plant S26, a sample of the seed of sesame plant S26 having been deposited under ATCC Patent Deposit Designation No. PTA-4317, wherein the regenerated sesame plant has all the physiological and morphological characteristics of sesame plant S26.

In another aspect, the present invention is a method of producing sesame seed, comprising crossing a first parent sesame plant with a second parent sesame plant, wherein the first or second parent sesame plant was produced by seed having been deposited under ATCC Patent Deposit Designation No. PTA-4317.

BRIEF DESCRIPTION OF DRAWINGS

FIG. 1 depicts the lineage of S26.

DETAILED DESCRIPTION

Figure 2:
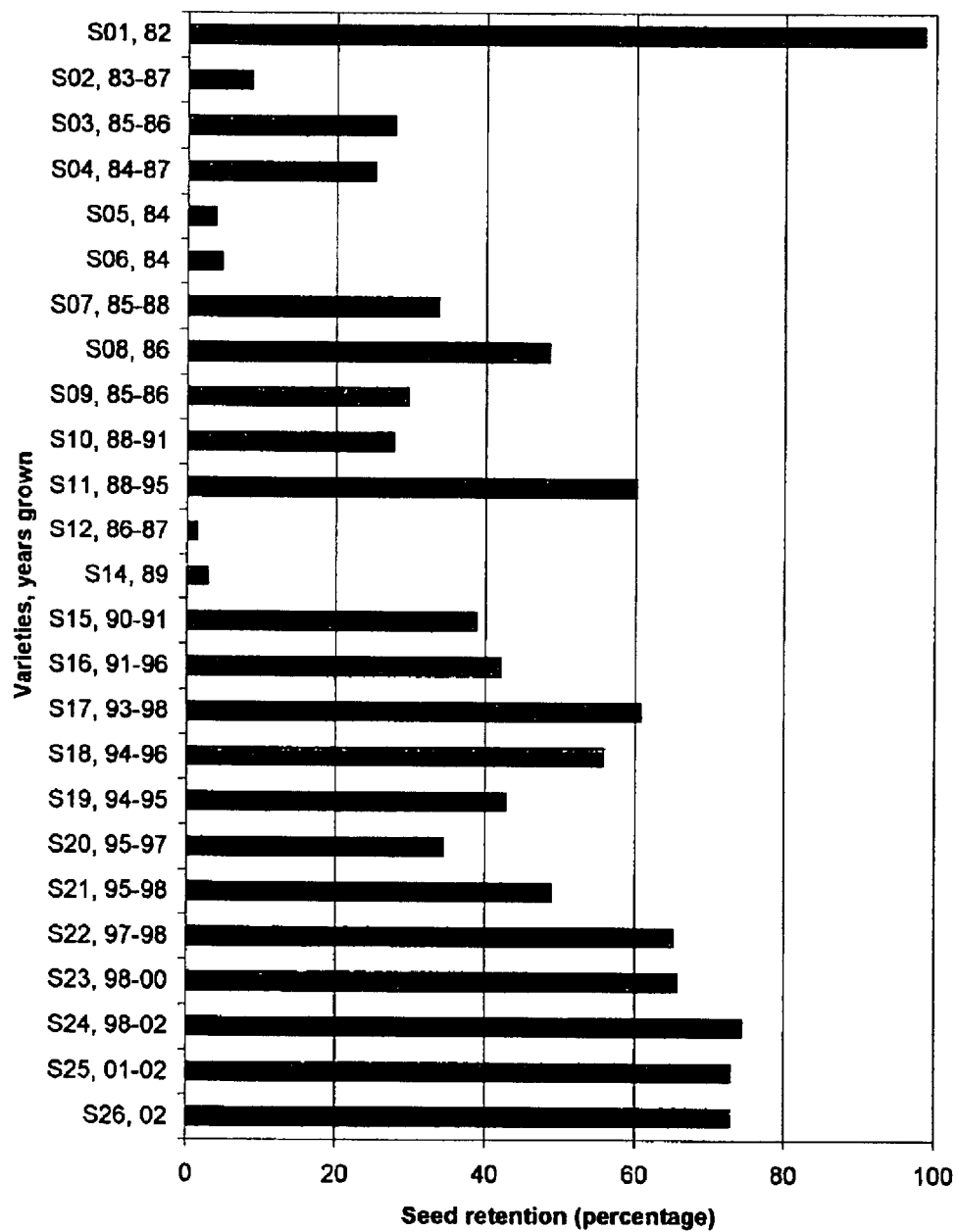
FIG. 2 depicts a comparison of the percent of seed retention during in shaker shatter resistance testing from 1997 to 2001 for sesame varieties released by Sesaco: Sesaco 01 (S01) released in 1982, Sesaco 02 (S02) released in 1983–1987, Sesaco 03 (S03) released in 1985–1986, Sesaco 04 (S04) released in 1984–1987, Sesaco 05 (S05) released in 1984, Sesaco 06 (S06) released in 1984, Sesaco 07 (S07) released in 1985–1988, Sesaco 08 (S08) released in 1986, Sesaco 09 (S09) released in 1985–1986, Sesaco 10 (S10) released in 1988–1991, Sesaco 11 (S11) released in 1988–1995, Sesaco 12 (S12) released in 1986–1987, Sesaco 14 (S14) released in 1989, Sesaco 15 (S15) released in 1990–1991, Sesaco 16 (S16) released in 1991–1996, Sesaco 17 (S17) released in 1993–1998, Sesaco 18 (S18) released in 1994–1996, Sesaco 19 (S19) released in 1994–1995, Sesaco 20 (S20) released in 1995–1997, Sesaco 21 (S21) released in 1995–1998, Sesaco 22 (S22) released in 1997–1998, Sesaco 23 (S23) released in 1998–2000, Sesaco 24 (S24) released in 1998–2002, Sesaco 25 (S25) released in 2001–2002, and Sesaco 26 (S26) released in 2002.

Sesame cultivar S26 (hereinafter "S26") is a non-dehiscent sesame variety having superior characteristics which make it a commercially suitable sesame line. S26 exhibits non-dehiscence as defined in U.S. Pat. No. 6,100, 452, the teachings of which are incorporated herein by reference, making it suitable for mechanized harvesting. In addition, S26 has more drought resistance which extends the planting region to areas with less rainfall, larger seed size which is desirable for processors, comparable shatter resistance, and improved resistance against common fungal diseases. With later maturity, S26 is more restricted on geographical range than the present varieties.

The recommended geographical area for S26 is from South Texas at the Rio Grande to central Oklahoma and from east Texas westward to elevations below 1,000 meters. S26 has not been tested in other states, but it is projected that it would perform well in New Mexico, Arizona, and California. S26 has not been exposed to the sesame diseases that have been reported east of Texas.

Sesaco used the pedigree method of plant breeding to develop S26. Sesame is generally self-pollinated. Crossing is done using standard techniques as delineated in Yermanos, D. M. 1980. "Sesame. Hybridization of crop plants," *Am Soc Agronomy-Crop Sci of America*, pp. 549–563 and U.S. Pat. No. 6,100,452. Ashri provides an overview of sesame breeding in Ashri, A. (1998). "Sesame breeding," *Plant Breed. Rev.* 16:179–228. When Sesaco started the U.S. breeding program in 1978, there were no two lines with all of the desirable characters for mechanization of sesame. Development of new varieties has depended on building blocks of desirable characters and then bringing in other blocks of desirable characters.

The lineage of S26 is presented in FIG. 1. 111 (1) was a line obtained from the National Plant Germplasm System (NPGS) (PI173955) in 1979 and first planted by Sesaco in the Woods nursery (Wellton, Ariz.) in 1981. NPGS obtained it in 1949 from W. N. Koelz, United States Department of Agriculture (USDA), Beltsville, Md. who obtained it from India. Within Sesaco, 111 first carried the identifier 0858 and was then changed to X111. In 1985, a selection of this line became Sesaco 4 (SO4).

111X (2) was an outcross in the plot BT0458 in the Nickerson nursery (Yuma, Ariz.) in 1982. Within Sesaco, it carried the identifier E0745.

F820 (3) was a cross made by Sesaco in the Nickerson nursery (Yuma, Ariz.) in 1982. Within Sesaco, it carried the identifier F820.

104 (4) was a line obtained from the Sesamum Foundation (D. G. Langham, Fallbrook, Calif.) in 1977 and first planted in the Kamman nursery (Wellton, Ariz.) in 1978. It was obtained with the designator SF084. The Sesamum Foundation obtained it from Maximo Rodriguez in 1961. He had collected it from Mexico where it was known as Instituto 8. Instituto 8 was a selection from G53.48, a cross made by D. G. Langham in 1953 in Guacara, Venezuela. Within Sesaco, 104 carried the identifier 0084. In 1982, a selection of this line became Sesaco 2 (SO2).

578 (5) was a cross made by Sesaco in the McElhaney nursery (Wellton, Ariz.) in 1983. Within Sesaco, it carried the identifier G8578 and then changed to T578.

F853 (6) was a cross made by Sesaco in the Nickerson nursery (Yuma, Ariz.) in 1982. Within Sesaco, it carried the identifier F853.

192 (7) was a line obtained from the M. L. Kinman in 1980 and first planted by Sesaco in the Woods nursery (Wellton, Ariz.) in 1981. The line was originally T61429-B-4-1-3 from the Kinman USDA sesame program, College Station, Tex., which had been in cold storage at Ft. Collins, Colo. In 1997, the line was transferred to the NPGS, Griffin, Ga. and given the identifier P1599462. Within Sesaco, 192 first carried the identifier 1479 and then was changed to X191 and X193. In 1985, a selection from X193 became Sesaco 3 (SO3) and a selection of X191 became Sesaco 7 (S07).

031 (8) was a cross made by Sesaco in the Ramsey nursery (Roll, Ariz.) in 1984. Within Sesaco, it carried the identifier H0031 and then changed to T031.

118 (9) was a line obtained from the NGPS (PI425944) in 1979 and first planted in Kamman nursery (Wellton, Ariz.) in 1979. The NGPS obtained it in 1978 from P. F. Knowles, University of California, Davis, Calif., who collected it in Pakistan. Within Sesaco, it carried the identifier 1118 and then changed to X118 and then to T118.

B1954 (10) was a cross made by Sesaco in the Gilleland nursery (Uvalde, Tex.) in 1993. Within Sesaco, it carried the identifier B1954.

72C (11) was a line obtained from the NGPS (PI292146) in 1979 and first planted in Woods nursery (Wellton, Ariz.) in 1981. The NGPS obtained it in 1963 from Hybritech Seed International, a unit of Monsanto, U.S., which obtained it from Israel. In viewing this material in 1986, A. Ashri of Israel concluded that it was an introduction to Israel. The material is similar to introductions from the Indian subcontinent. Within Sesaco, it has carried the identifier 0702 and then changed to X702 and then to X702C. In 1986, a selection from X702C became Sesaco 12 (S12).

L6651 (12) was a cross made by Sesaco in the Wright nursery (Roll, Ariz.) in 1987. Within Sesaco, it carried the identifier L6651.

G8 (13) was a line obtained from D. G. Langham in 1977 and first planted by Sesaco in the Kamman nursery (Wellton, Ariz.) in 1978. It was a selection from the cultivar 'Guacara' which D. G. Langham developed in Venezuela in the 1950s. Guacara was an initial selection from a cross that later produced one of the major varieties in Venezuela—Aceitera. Within Sesaco, G8 first carried the identifier X011 and was later changed to TG8.

804 (14) was a cross made by Sesaco in the Nickerson nursery (Yuma, Ariz.) in 1982. Within Sesaco, it has carried the identifier F804; in 1988, a selection of this line became Sesaco 11 (S11).

2CA (15) was a cross made by Sesaco in the Wright nursery (Roll, Ariz.) in 1988. Within Sesaco, it has carried the identifier LCX02 and later changed to X2CA and then to T2CA.

S11 (16) was a cross made by Sesaco in the Nickerson nursery (Yuma, Ariz.) in 1982. Within Sesaco, it carried the identifier F804. In 1988, a selection of this line became Sesaco 11 (S11).

SOMALIA (17) was a line obtained from the NGPS (PI210687) in 1979 and first planted in Kamman nursery (Wellton, Ariz.) in 1979. The NGPS obtained it from the Administrazione Fiduciaria Italiana della Somalia, Mogadishu, Somalia. Within Sesaco, it carried the identifier 0730.

H6778 (18) was a cross made by Sesaco in the Hancock nursery (Wellton, Ariz.) in 1984. Within Sesaco, it carried the identifier H6778.

J3208 (19) was a cross made by Sesaco in the Hancock nursery (Wellton, Ariz.) in 1985. Within Sesaco, it carried the identifier J3208.

193 (20) was a selection from 192 (7) described above. Within Sesaco, it carried the identifier X193. In 1985, a selection of X193 became Sesaco 03 (S03).

H6432 (21) was a cross made by Sesaco in the Hancock nursery (Wellton, Ariz.) in 1984. Within Sesaco, it carried the identifier H6432.

MAX (22) was a line obtained from the Sesamum Foundation (D. G. Langham, Fallbrook, Calif.) in 1977 and first planted in the Kamman nursery (Wellton, Ariz.) in 1978. The Sesamum Foundation obtained it from Maximo Rodriguez in 1961. He had collected it from Mexico where it was known as Instituto Regional Canasta. Within Sesaco, it carried the identifier 0116 and then changed to TMAX.

076 (23) was a cross made by Sesaco in the Kamman nursery (Wellton, Ariz.) in 1979. Within Sesaco, it carried the identifier C076 and then changed to T076.

R234 (24) was a named variety obtained from D. M. Yermanos in 1978 from his sesame program at the University of California at Riverside. It was first planted in the Kamman nursery (Wellton, Ariz.) in 1978. Within Sesaco, it carried the identifier 0544 and then changed to T234.

R234 TALL (25) was an outcross found in the Kamman nursery (Wellton, Ariz.) in 1979. Within Sesaco, it carried the identifier X026.

K3255 (26) was a cross made by Sesaco in the Hancock nursery (Wellton, Ariz.) in 1986. Within Sesaco, it carried the identifier K3255.

045 (27) was a cross made by Sesaco in the Kamman nursery (Wellton, Ariz.) in 1978. Within Sesaco, it carried the identifier B045 and then changed to T045.

G958-1 (28) was a line obtained from the Sesamum Foundation in 1977 and first planted in the Kamman nursery (Wellton, Ariz.) in 1978. It was obtained with a designator of SF411. The Sesamum Foundation obtained it from John Martin in 1962 who had obtained it from the D. G. Langham breeding program in Venezuela. Within Sesaco, G958-1 carried the identifier 0411.

H6785 (29) was a cross made by Sesaco in the Hancock nursery (Wellton, Ariz.) in 1984. Within Sesaco, it carried the identifier H6785.

982 (30) was a line obtained from the Sesamum Foundation in 1977 and first planted in the Kamman nursery (Wellton, Ariz.) in 1978. It was obtained with a designator of SF477 and was named G53.98-2. The Sesamum Foundation obtained it from John Martin in 1962 who had obtained it from the D. G. Langham breeding program in Venezuela. G53.98-2 was a cross made by D. G. Langham in 1953 in Guacara, Venezuela. Within Sesaco, 982 carried the identifier 0477 and then changed to T982.

036 (31) was a cross made by Sesaco in the Kamman nursery (Wellton, Ariz.) in 1979. Within Sesaco, it carried the identifier CO36 and then X036. In 1984, a selection from X036 became Sesaco 6 (SO6).

G53.80-1 (32) was a line obtained from the Sesamum Foundation in 1977 and first planted in the Kamman nursery (Wellton, Ariz.) in 1978. It was obtained with a designator of SF471. The Sesamum Foundation obtained it from John Martin in 1962 who had obtained it from the D. G. Langham breeding program in Venezuela. G53.80-1 was a cross made by D. G. Langham in 1953 in Guacara, Venezuela. Within Sesaco, G53.80-1 carried the identifier 0471.

J3222 (33) was a cross made by Sesaco in the Hancock nursery (Wellton, Ariz.) in 1985. Within Sesaco, it carried the identifier J3222.

195 (34) was an outcross selected in plot MN4584 in the McElhaney nursery (Wellton, Ariz.) in 1983. Within Sesaco, it carried the identifier E0690 and then changed to X195.

H6562 (35) was a cross made by Sesaco in the Hancock nursery (Wellton, Ariz.) in 1984. Within Sesaco, it carried the identifier H6562.

701 (36) was a line obtained from the NGPS (PI292145) in 1979 and first planted in Woods nursery (Wellton, Ariz.) in 1981. The NGPS obtained it in 1963 from Hybritech Seed International, a unit of Monsanto, U.S., which obtained it from Israel. In viewing this material in 1986, A. Ashri of Israel concluded that it was an introduction to Israel. The material is similar to introductions from the Indian subcontinent. Within Sesaco, it carried the identifier 0701 and then changed to X701. In 1984, a selection from X701 became Sesaco 5 (SO5).

S16 (37) was a cross made by Sesaco in the Wright nursery (Roll, Ariz.) in 1987. Within Sesaco, it carried the identifier KAP11 and then changed to XFXA. In 1991, a selection from XFXA became Sesaco 16 (S16).

S26 (38) was a cross made by Sesaco in the Friesenhahn nursery (Knippa, Tex.) in 1994. The original designator was CM764. The seed (M764) from the cross was planted in plot E082 in the Friesenhahn nursery (Knippa, Tex.) in 1995. Four plants were selected based on "031 genes, a good phenotype, and good kill resistance." The seed (2717) from one of the plants was planted in plot 2067 in the Gilleland nursery (Uvalde, Tex.) in 1996. Six plants were selected based on "good low height of the first capsule and producing a wide row." The seed (1375) from one of the plants was planted in plot 4677 in the Gilleland nursery (Uvalde, Tex.) in 1997. Nineteen plants were selected based on "good kill resistance, wide row, lot of capsules in the row, light seeking ability, and bottom regrowth." The identifier was changed to X13J. The seed (3240) from one of the plants was planted in plot 0213 in the Gilleland nursery (Uvalde, Tex.) in 1998. Five plants were selected based on "good branches, lot of capsules, wide row, and capability of growing on 101 cm rows." The seed (2838) from one of the plants was planted in plot F211 in the Meeks nursery (Tipton, Okla.) in 1999. A bulk of 22 plants was selected based on "a prayer leaf, very wide row, lot of capsules plus, and the turn-off gene." The bulk seed (7635) was planted in a strip (VE17) next to the Schwartz nursery (Wall, Tex.) in 2000. The strip was combined. The combined seed was tested on two farms: the Schwartz farm (Wall, Tex.) and Michalewicz farm (Water Valley, Tex.) in 2001, and the seed combined. The combined seed was released to farmers in May, 2002.

Along with breeding programs, tissue culture of sesame is currently being practiced in Korea, Japan, Sri Lanka and the United States. It is possible for one of ordinary skill in the art to utilize sesame plants grown from tissue culture as parental lines in the production of non-dehiscent sesame. Further, it is possible to propagate non-dehiscent sesame through tissue culture methods. By means well known in the art, sesame plants can be regenerated from tissue culture having all the physiological and morphological characteristics of the source plant.

The present invention includes the seed deposited under ATCC Patent Deposit Designation No. PTA-4317; a plant, designated as S26, or parts thereof which are produced by the seed deposited under ATCC Patent Deposit Designation No. PTA-4317; seed produced by plant S26 or its progeny having the physiological and morphological characteristics of sesame plant S26 or a plant produced by the seed deposited under ATCC Patent Deposit Designation No. PTA-4317; any plant having plant S26 as a parent, and any plant having the physiological and morphological characteristics of sesame plant S26 or a plant produced by the seed deposited under ATCC Patent Deposit Designation No. PTA-4317. The present invention also includes a tissue culture of seed having been deposited under ATCC Patent Deposit Designation No. PTA-4317 or a tissue culture of sesame plant S26 or its parts, a sample of the seed of sesame plant S26 having been deposited under ATCC Patent Deposit Designation No. PTA-4317. A sesame plant regenerated from a tissue culture of a seed having been deposited under ATCC Patent Deposit Designation No. PTA-4317 or from sesame plant S26, wherein the regenerated sesame plant has all the physiological and morphological characteristics of a sesame plant produced by the seed deposited under ATCC Patent Deposit Designation No. PTA-4317 is also contemplated by the present invention. Methods of producing sesame seed, comprising crossing a first parent sesame plant with a second parent sesame plant, wherein the first or second parent sesame plant was produced by seed having been deposited under ATCC Patent Deposit Designation No. PTA-4317 are part of the present invention.

Unless otherwise stated, as used herein, the term plant includes plant cells, plant protoplasts, plant cell tissue cultures from which sesame plants can be regenerated, plant calli, plant clumps, plant cells that are intact in plants, or parts of plants, such as embryos, pollen, ovules, flowers, capsules, stems, leaves, seeds, roots, root tips, and the like. Further, unless otherwise stated, as used herein, the term progeny includes plants derived from plant cells, plant protoplasts, plant cell tissue cultures from which sesame plants can be regenerated, plant calli, plant clumps, plant cells that are intact in plants, or parts of plants, such as embryos, pollen, ovules, flowers, capsules, stems, leaves, seeds, roots, root tips, and the like.

Sesame cultivar S26 has been extensively grown in the following three nurseries:

(1) Uvalde nursery planted north of Uvalde, Tex. (latitude 29°22' north, longitude 99°47' west, 226 m elev) in middle to late May from 1988–2001; mean rainfall is 608 mm annually with a mean of 253 mm during the growing season; temperatures range from an average low of 3° C. and an average high of 17° C. in January to an average low of 22° C. and an average high of 37° C. in July. The nursery was planted on 96 cm beds from 1988 to 1997 and on 76 cm beds from 1998 to 2001. The nursery was pre-irrigated and has had 2–3 post-plant irrigations depending on rainfall. The fertility has varied from 30–60 units of nitrogen.

(2) San Angelo nursery planted east of San Angelo, Tex. (latitude 31°21' north, longitude 100°30' west, 908 m elev) in early to middle June from 1992–2001; mean rainfall is 490 mm annually with a mean of 201 mm during the growing season; temperatures range from an average low of 0° C. and an average high of 15° C. in January to an average low of 22° C. and an average high of 36° C. in July. The nursery was planted on 101 cm beds. The nursery was pre-irrigated in years when there was no planting rain and has had 0 to 1 post-plant irrigations depending on rainfall. The fertility has varied from 20–50 units of nitrogen.

(3) Oklahoma nursery planted north of Tipton, Okla. (latitude 34°28' north, longitude 99°10' west, 380 m elev) from middle June to early July from 1998–2001; mean rainfall is 630 mm annually with a mean of 251 mm during the growing season; average daily temperatures range from an average low of −3° C. and an average high of 9° C. in January and an average low of 23° C. low and an average high of 36° C. in July. The nursery was planted in the first two years on 101 cm beds and the last two on 91 cm beds. The nursery was pre-irrigated in years when there was no planting rain and has had 0 to 2 post-plant irrigations depending on rainfall. The fertility has varied from was 30–50 units of nitrogen.

Sesame cultivar S26 has shown uniformity and stability within the limits of environmental influence for the characters listed in Table I below. Table I provides the name, definition, and rating scale of each character as well as the method by which the character is measured. Under the rating section, the rating for S26 is presented in bold text. Additionally, the distribution of the character in Sesaco's sesame development program is indicated under the rating section. Sesaco uses slightly different character specifications from "Descriptors for sesame", AGP:IBPGR/80/71, IBPGR Secretariat, Rome, (1981) and from the form "Sesame (*Sesamum indicum*)", U.S. Department of Agriculture Plant Variety Protection Office, Beltsville, Md. The descriptors in those documents were developed in the early 1980s and have not been updated to incorporate new concepts in sesame data collection.

TABLE I

Characters Distinguishing the S26 Line

| Character | Rating | Methodology |
|---|---|---|
| (1) BRANCHING STYLE<br>The potential amount of true branching in a line | Subjective rating<br>Values:<br>U = Uniculm-no branching except weak branches in open<br>B = True branches<br>S26 = B for all crops in all nurseries<br>Distribution within Sesaco based on stable lines in the crossing program in 1982–2001 (Total number of samples tested = 1,333)<br>U = 42.4%<br>B = 57.6% | The amount of branching on any particular plant depends on the space around the plant. In high populations, branching can be suppressed. This rating should be based on potential as expressed on end plants and plants in the open. True branches start in the leaf axil below the first flower, and they begin to emerge before the first open flower. As long as there is light into the leaf axils, there will be additional branches that start below the first branches in subsequently lower nodes. Weak branches occur when a plant is in the open. They develop in the lowest nodes and subsequent branches start at higher nodes. There are lines that will not branch in any circumstance. Some lines in the open will put on spontaneous branches late in the cycle. True and weak branches do not have a capsule in the same leaf axil, whereas the spontaneous branches form under the capsule after the capsule has formed. Spontaneous branches are |

TABLE I-continued

Characters Distinguishing the S26 Line

| Character | Rating | Methodology |
|---|---|---|
| | | not counted as branches. There are rare lines where the flowering pattern is to put on flowers on lower nodes late in the cycle. In this case, the capsule is formed after the branch is developed. This pattern should not be termed spontaneous branching, and the branch is normally counted as a true branch. There are branched lines that have secondary branches on the branches. In a few cases, there can be tertiary branches. Additional branches generally appear in low populations. Comments: the effects of light appear to have more of an effect on branching than moisture and fertility. High populations suppress branching. |
| (2) NUMBER OF CAPSULES PER LEAF AXIL The predominant number of capsules per leaf axil in the middle half of the capsule zone | Subjective rating Values: 1 = Single 3 = Triple Based on potential as described in the methodology presented herein S26 = 1 for all crops in all nurseries Distribution within Sesaco based on stable lines in the crossing program in 1982-2001 (Total number of samples tested = 1,327) 1 = 58.3% 3 = 41.7% | Rating can be taken from about 60 days after planting through to the end of the crop. Number of Capsules per Leaf Axil is highly dependent on moisture, fertility, and light. In triple capsule lines, the central capsule forms first, and axillary capsules follow a few days later. Triple capsule lines have the potential to put on axillaries, but will not do so if plants do not have adequate moisture and/or fertility. In drought conditions, some triple capsule lines will produce only a central capsule for many nodes. In these lines, when there is adequate moisture through rain or irrigation, some will add axillary capsules on only new nodes, while others will add axillary capsules to all nodes. Some triple capsule lines will not put on axillary capsules if there is no direct sunlight on the leaf axil. To date, lines with single capsules have nectaries next to the central capsule in the middle of the capsule zone while triple capsules do not. However, some lines have what appear to be nectaries on the lower capsules of triple lines, but upon close examination, they are buds which may or may not eventually develop into a flower and then a capsule. In most triple capsule lines, the lower and upper nodes have single capsules. There are some lines where the end plants can put on 5 capsules/leaf axil and a few that have the potential to put on 7 capsules/leaf axil. 5 and 7 capsules only appear with open plants with high moisture and fertility. In some environments, single capsule lines will put on multiple capsules on 1 node and rarely on up to 5 nodes. These lines are not considered triple capsule lines. |
| (3) MATURITY CLASS The maturity of a line in relation to a standard line. Currently, the standard line is S24 at 95 days | Subjective rating Values: V = Very early (<85 days) E = Early (85–94 days) M = Medium (95–104 days) L = Late (105–114 days) T = Very late (>114 days) S26 = M in 1998–2001 in Uvalde nursery[a] Distribution within Sesaco based on stable lines in the crossing program in 1998–2001 (Total number of samples tested = 650) V = 1.2% E = 26.8% M = 56.2% L = 12.9% T = 2.9% | The basis for this data point is Days to Physiological Maturity (Character No. 27). S24 is the standard line to be used to compute Maturity Class. In 1998–2001, the maturity of S24 averaged 95 days in the Uvalde, TX, nursery. For each line, the physiological maturity for each year is subtracted by the S24 maturity for that year in that nursery, and then the number of days of difference is averaged. The average is then added to 95. See Days to Physiological Maturity (Character No. 27) for the effects of the environment on Maturity Class. |
| (4) PLANT PHENOTYPE A three character | Subjective rating Values: Branching Style | The first character is the Branching Style (Character No. 1), followed by the Number of Capsules per Leaf Axil (Character No. 2), and |

TABLE I-continued

Characters Distinguishing the S26 Line

| Character | Rating | Methodology |
|---|---|---|
| designation that provides the branching style, number of capsules per leaf axil, and the maturity class | U = Uniculm-no branching except weak branches in open<br>B = True branches<br>Number of Capsules per Leaf Axil<br>1 = Single<br>3 = Triple<br>Maturity Class<br>V = Very early (<85 days)<br>E = Early (85–94 days)<br>M = Medium (95–104 days)<br>L = Late (105–114 days)<br>T = Very late (>114 days)<br>S26 = B1M for all crops in all nurseries<br>Distribution within Sesaco based on stable lines in the crossing program in 1998–2001 (Total number of samples tested = 650)<br>U1V = 0%        U3V = 1.1%<br>U1E = 3.8%     U3E = 8.3%<br>U1M = 16.0%   U3M = 12.0%<br>U1L = 3.4%     U3L = 2.2%<br>U1T = 0.5%     U3T = 0.6%<br>B1V = 0%        B3V = 0.2%<br>B1E = 8.0%     B3E = 6.3%<br>B1M = 23.2%   B3M = 4.8%<br>B1L = 6.5%     B3L = 1.0%<br>B1T = 1.6%     B3T = 0.4% | then the Maturity Class (Character No. 3). When these characters are placed in a matrix, there are 20 potential phenotypes. The phenotype provides an overview of the general appearance of the plant. There is a very high correlation between Maturity Class and Height of Plant (Character No. 5). |
| (5) HEIGHT OF PLANT<br>The height of the plant from the ground to the top of the highest capsule with viable seed | Unit of measure: cm<br>Values: average of 3 plants<br>S26 = 128 cm in 2000 in Uvalde nursery and 144 cm in 2001 in Uvalde nursery<br>Distribution within Sesaco based on stable lines in the crossing program in 1999–2001 (Total number of samples tested = 2274)<br>low = 56 cm   high = 249 cm<br>1 = <94.6 cm; 5.2%<br>2 = <133.2 cm; 34.6%<br>3 = <171.8 cm; 54.9%<br>4 = <210.4 cm; 5.1%<br>5 = >210.3 cm; 0.1%<br>avg. = 134.8 cm, std = 23.5 | The measurement is made after the plants stop flowering. For plants that are not erect or have lodged, the plant should be picked up for the measurement. In most lines the highest capsule is on the main stem. In lines with the dt/dt alleles (determinate), the highest capsule is on the branches.<br>Comments: this height is dependent on the amount of moisture, heat, fertility, and population. Increased values generally increase the height. In a high population, the height will only increase if there is adequate fertility and moisture; otherwise, the height will be shorter. In low light intensities, the heights are generally taller. |
| (6) HEIGHT OF FIRST CAPSULE<br>The height of the first capsule from the ground to the bottom of the lowest capsule on the central stem | Unit of measure: cm<br>Values: average of 3 plants<br>S26 = 53 cm in 2000 in Uvalde nursery and 50 cm in 2001 in Uvalde nursery<br>Distribution within Sesaco based on stable lines in the crossing program in 1999-2001 (Total number of samples tested = 2274)<br>low = 20 cm   high = 193 cm<br>1 = <54.6 cm; 52.7%<br>2 = <89.2 cm; 45.5%<br>3 = <123.8 cm; 1.5%<br>4 = <158.4 cm; 0.3%<br>5 = >158.3 cm; 0.1%<br>avg. = 54.2 cm, std = 14.3 | The measurement is made after the plants stop flowering. For plants that are not erect or have lodged, the plant should be picked up for the measurement. In most lines, the lowest capsule is on the main stem. True branches have capsules higher than on the main stem except when the flowers fall off. Occasionally, on weak branches, the lowest capsule is on the branches.<br>There are lines that flower in the lower nodes late in the cycle, and, thus, the measurement should be taken after flowering ends. In many lines the first flower does not make a capsule, and, thus, this height may not be the same as the height of the first flower. The height is correlated to the length of time to flowering, the earlier the lower the height.<br>Comments: see Height of Plant (Character No. 5) for effects of environmental factors |
| (7) CAPSULE ZONE LENGTH<br>The length of the capsule zone. The capsule zone extends from the bottom of the lowest capsule on the main stem to the top of the highest capsule on | Unit of measure: cm<br>Values: average of 3 plants<br>S26 = 75 cm in 2000 in Uvalde nursery and 94 cm in 2001 in Uvalde nursery<br>Distribution within Sesaco based on stable lines in the crossing program in 1999– | The measurement is derived by subtracting the Height of First Capsule (Character No. 6) from the Height of Plant (Character No. 5).<br>Comments: see Height of Plant (Character No. 5) for effects of environmental factors |

TABLE I-continued

Characters Distinguishing the S26 Line

| Character | Rating | Methodology |
|---|---|---|
| the main stem. | 2001 (Total number of samples tested = 2274) low = 18 cm  high = 188 cm 1 = <52 cm; 4.7% 2 = <86 cm; 53.5% 3 = <120 cm; 41.3% 4 = <154 cm; 0.5% 5 = >153.9 cm; 0.1% avg. = 80.6 cm, std = 17.2 | |
| (8) NUMBER OF CAPSULE NODES The number of capsule nodes from the lowest capsule node to the highest node with capsules with viable seed on the main stem of the plant | Unit of measure: number Values: average of 3 plants S26 = 23 in 2000 in Uvalde nursery and 29 in 2001 in Uvalde nursery Distribution within Sesaco based on stable lines in the crossing program in 1999–2001 (Total number of samples tested = 2154) low = 10   high = 54 1 = <18.8; 17.9% 2 = <27.6; 48.3% 3 = <36.4; 29.5% 4 = <45.2; 3.6% 5 = >45.1; 0.7% avg. = 25.3, std = 6.4 | The count is made after the plants stop flowering. On alternate arranged leaves, each pair of leaves is counted as one node. In some lines, there are three leaves per node for at least part of the plant. In some plants, flowers may not have produced capsules on one or more of the leaf axils in a node. These nodes should still be counted. Nodes on the branches are not counted. In years when the amount of moisture available to the plant is irregular, nodes can become very irregular, particularly on triple capsule lines. In the upper portions of the plant, it may become easier to count the capsule clusters and divide by 2. While it is possible to count nodes after leaves have fallen, it is much easier to count while the leaves are still on the plant. Comments: the number of nodes is dependent on the amount of moisture and fertility. Higher moisture and fertility increases the number of nodes. |
| (9) AVERAGE INTERNODE LENGTH WITHIN CAPSULE ZONE The average internode length within the capsule zone | Unit of measure: cm Values: average of 3 plants S26 = 3.3 cm in 2000 in Uvalde nursery and 3.3 cm in 2001 in Uvalde nursery Distribution within Sesaco based on stable lines in the crossing program in 1999–2001 (Total number of samples tested = 2145) low = 1.09 cm high = 8.09 cm 1 = <2.49 cm; 6.2% 2 = <3.89 cm; 74.6% 3 = <5.29 cm; 18.6% 4 = <6.69 cm; 0.4% 5 = >6.68 cm; 0.1% avg. = 3.35 cm, std = 0.66 | Divide the Capsule Zone Length (Character No. 7) by the Number of Capsule Nodes (Character No. 8). Comments: this length is dependent on the amount of moisture, fertility, and population. Increased values generally increase the length. In a high population, the length will only increase if there is adequate fertility and moisture; otherwise the length will be shorter. In low light intensities, the lengths are generally longer. Past methodologies have measured the internode length at the middle of the capsule zone. Some have measured it at the median node and others at the median Capsule Zone Length. |
| (10) YIELD AT DRYDOWN An extrapolation of the yield of a field by taking sample yields | Unit of measure: kg/ha Values: average of 3 replications S26 = 1421 kg/ha in 2000 in Uvalde nursery; 1696 kg/ha in 2001 in Uvalde nursery; 390 kg/ha in 2000 in San Angelo nursery[b]; and 1611 kg/ha in 2001 in San Angelo nursery Distribution within Sesaco based on stable lines in the crossing program in 1999–2001 (Total number of samples tested = 1828) low = 67 kg/ha high = 2421 kg/ha 1 = <537.8 kg/ha; 5.6% 2 = <1008.6 kg/ha; 15.6% 3 = <1479.4 kg/ha; 51.5% 4 = <1950.2 kg/ha; 25.8% 5 = >1950.1 kg/ha; 1.4% avg. = 1114.6 kg/ha, std = 331.2 | On 3 replicated plots, when the plants are dry enough for direct harvest, cut a minimum of 1/5000 of a hectare (Sesaco uses 1/2620) in the plot and place the plants in a cloth bag. Thresh the sample in a plot thresher and weigh the seed. Multiply the weight by the appropriate multiplier based on area taken to provide the extrapolated yield in kg/ha. In the Almaco thresher there is about 3% trash left in the seed. Since yields are comparative, there is no cleaning of the seed done before the computation. If other threshers have more trash, the seed should be cleaned before weighing. Comments: yields increase with moisture and fertility. However, too high a moisture can lead to killing of plants. Too high fertility can lead to extra vegetative growth that may not lead to higher yields. The optimum population depends on the phenotype (Branching Style, Character No. 1; Number of Capsules per Leaf Axil, Character No. 2; and Maturity Class, Character No. 3) and row width. |
| (11) RESISTANCE TO DROUGHT | Subjective rating Values: 0 to 8 scale | In a year when there is a drought, this rating can be used to differentiate the effects of the |

TABLE I-continued

Characters Distinguishing the S26 Line

| Character | Rating | Methodology |
|---|---|---|
| The relative amount of resistance to drought | 7 = Little effect from drought<br>4 = Medium effect from drought<br>1 = Considerable effect from drought<br>Intermediate values are used.<br>S26 = 6.4 in 2000 in San Angelo nursery<br>Distribution within Sesaco based on stable lines in the crossing program in 2000 (Total number of samples tested = 632)<br>low = 0  high = 8<br>1 = <1.6; 0.8%<br>2 = <3.2; 28.0%<br>3 = <4.8; 36.1%<br>4 = <6.4; 34.5%<br>5 = >6.3; 0.6%<br>avg. = 4.1, std = 1.2 | different lines. This is a highly subjective rating requiring a rater that is familiar with the performance of the line under normal conditions. The rating is based on how the drought changes the line from normal. Thus, a short line that does not change significantly in a drought may have a higher rating than a tall line which is affected by the drought even though the taller line is taller in the drought than the short line. |
| (12) LEAF LENGTH<br>The length of the leaf blade from the base of the petiole to the apex of the leaf from the $5^{th}$, $10^{th}$, and $15^{th}$ nodes | Unit of measure: cm<br>Values: average of 3 plants<br>S26 = 30.4 cm for $5^{th}$ node in 2001 in San Angelo nursery; 20.1 cm for $10^{th}$ node in 2001 in San Angelo nursery; and 18.6 cm for $15^{th}$ node in 2001 in San Angelo nursery<br>Distribution within Sesaco for $5^{th}$ leaf based on stable lines in the crossing program in 2001 (Total number of samples tested = 100)<br>low = 15.9 cm<br>high = 55.5 cm<br>1 = <23.8 cm; 41%<br>2 = <31.7 cm; 44%<br>3 = <39.7 cm; 12%<br>4 = <47.6 cm; 1%<br>5 = >47.5 cm; 2%<br>avg. = 26.1 cm, std = 6.8<br>Distribution within Sesaco for $10^{th}$ leaf based on stable lines in the crossing program in 2001 (Total number of samples tested = 100)<br>low = 12.0 cm<br>high = 53.5 cm<br>1 = <20.3 cm; 48%<br>2 = <28.6 cm; 40%<br>3 = <36.9 cm; 8%<br>4 = <45.2 cm; 3%<br>5 = >45.1 cm; 1%<br>avg. = 21.9 cm, std = 6.7<br>Distribution within Sesaco for $15^{th}$ leaf based on stable lines in the crossing program in 2001 (Total number of samples tested = 59)<br>low = 10.0 cm<br>high = 49.5 cm<br>1 = <17.9 cm; 54.2%<br>2 = <25.8 cm; 37.3%<br>3 = <33.7 cm; 6.8%<br>4 = <41.6 cm; 0%<br>5 = >41.5 cm; 1.7%<br>avg. = 18.6 cm, std = 6.1 | Select one leaf per node to measure from the $5^{th}$, $10^{th}$, and $15^{th}$ nodes from the base of the plant. All the leaves for one line should be collected at the same time. Some lines retain the cotyledons, and the cotyledon node does not count as a node. In some lines the lowest leaves abscise leaving a scar on the stem. Abscised nodes should be counted. In lines with alternate leaves, one node is counted for each pair of leaves. In some lines in parts of the plant there are three leaves per node which should be counted as one node.<br>The leaves continue growing in the first few days after they have separated from the growing tip. The choosing of leaves should be done a minimum of 5 days after the $15^{th}$ node has appeared. Timing is important, because the plants will begin to shed their lower leaves towards the end of their cycle.<br>There are lines that have less than 15 nodes. In this case, the highest node should be taken and the node number annotated to the measurements.<br>There can be as much as 6 mm difference between a green leaf and a dry leaf. The measurements can be done on a green or dry leaf as long as any comparison data with other lines is based on the same method.<br>Generally, the lowest leaves increase in size until the $4^{th}$ to $6^{th}$ node and then they decrease in size. This applies to all measurements (Leaf Length (Character No. 12), Leaf Blade Length Character No. 13), Leaf Blade Width (Character No. 14), and Petiole Length (Character No. 15). Generally, the width will decrease at a greater rate than the length.<br>Comments: the length is dependent on the amount of moisture and fertility. Higher moisture and fertility increase the length. Leaf size also appears to be affected by light intensity. In Korea, the Korean lines have much larger leaves than in Oklahoma. In Korea, there is more cloud cover and a general haze than in Oklahoma.<br>The largest leaves are on photosensitive lines which when planted in the tropics fall into the $2^{nd}$ and $3^{rd}$ class |
| (13) LEAF BLADE LENGTH<br>The length of the leaf blade from the base of the leaf blade to the apex of the leaf from the $5^{th}$, $10^{th}$, and $15^{th}$ nodes | Unit of measure: cm<br>Values: average of 3 plants<br>S26 = 17.1 cm for $5^{th}$ node in 2001 in San Angelo nursery; 14.1 cm for $10^{th}$ node in 2001 in San Angelo nursery; and 14.4 cm for | See Leaf Length (Character No. 12) on how to collect leaves. The measurement does not include Petiole Length (Character No. 15). In some leaves the blade on one side of the petiole starts before the other side. This measure should start from the lowest blade side. There are leaves that have enations where a blade |

TABLE I-continued

Characters Distinguishing the S26 Line

| Character | Rating | Methodology |
|---|---|---|
| | 15$^{th}$ node in 2001 in San Angelo nursery<br>Distribution within Sesaco for 5$^{th}$ leaf based on stable lines in the crossing program in 2001 (Total number of samples tested = 100)<br>low = 10.0 cm<br>high = 31.0 cm<br>1 = <14.2 cm; 30%<br>2 = <18.4 cm; 43%<br>3 = <22.6 cm; 22%<br>4 = <26.8 cm; 2%<br>5 = >26.7 cm; 3%<br>avg. = 16.4 cm, std = 3.7<br>Distribution within Sesaco for 10$^{th}$ leaf based on stable lines in the crossing program in 2001 (Total number of samples tested = 100)<br>low = 9.8 cm<br>high = 30.1 cm<br>1 = <13.9 cm; 30%<br>2 = <17.9 cm; 43%<br>3 = <22.0 cm; 19%<br>4 = <26.0 cm; 6%<br>5 = >25.9 cm; 2%<br>avg. = 16.1 cm, std = 3.9<br>Distribution within Sesaco for 15$^{th}$ leaf based on stable lines in the crossing program in 2001 (Total number of samples tested = 59)<br>low = 8.5 cm<br>high = 27.5 cm<br>1 = <12.3 cm; 28.8%<br>2 = <16.1 cm; 42.4%<br>3 = <19.9 cm; 20.3%<br>4 = <23.7 cm; 5.1%<br>5 = >23.6 cm; 3.4%<br>avg. = 14.7 cm, std = 3.7 | starts and then stops. The enations are not considered part of the leaf blade because they are very irregular from plant to plant and within a plant.<br>Comments: see Leaf Length (Character No. 12) for effects of environment<br>The largest leaves are on photosensitive lines which when planted in the tropics fall into the 2$^{nd}$ and 3$^{rd}$ class |
| (14) LEAF BLADE WIDTH<br>The width of the leaf blade measured across the leaf blade at the widest point at the 5$^{th}$, 10$^{th}$, and 15$^{th}$ nodes | Unit of measure: cm<br>Values: average of 3 plants<br>S26 = 19.5 cm for 5$^{th}$ node in 2001 in San Angelo nursery; 6.5 cm for 10$^{th}$ node in 2001 in San Angelo nursery; and 3.2 cm for 15$^{th}$ node in 2001 in San Angelo nursery<br>Distribution within Sesaco for 5$^{th}$ leaf based on stable lines in the crossing program in 2001 (Total number of samples tested = 100)<br>low = 2.3 cm<br>high = 46.0 cm<br>1 = <11.0 cm; 52%<br>2 = <19.8 cm; 36%<br>3 = <28.5 cm; 10%<br>4 = <37.3 cm; 1%<br>5 = >37.4 cm; 1%<br>avg. = 12.3 cm, std = 6.5<br>Distribution within Sesaco for 10$^{th}$ leaf based on stable lines in the crossing program in 2001 (Total number of samples tested = 100)<br>low = 1.8 cm<br>high = 37.0 cm<br>1 = <8.8 cm; 91%<br>2 = <15.5 cm; 6%<br>3 = <22.9 cm; 1%<br>4 = <29.9 cm; 1%<br>5 = >29.8 cm; 1% | See Leaf Length (Character No. 12) on how to collect leaves. There are many leaves that are not symmetrical with lobbing on one side and not the other. The width should still be measured across the widest point on a line perpendicular to the main vein of the leaf.<br>On some lines the width exceeds the length, particularly on lobed leaves.<br>Comments: see Leaf Length (Character No. 12) for effects of environment<br>The largest leaves are on photosensitive lines which when planted in the tropics fall into the 2$^{nd}$ and 3$^{rd}$ class. The widest leaves are lobed. Normally, the leaves have turned from lobed to lanceolate by the 10$^{th}$ leaf with the exception of the tropical lines. |

TABLE I-continued

Characters Distinguishing the S26 Line

| Character | Rating | Methodology |
|---|---|---|
| | avg. = 5.5 cm, std = 4.7<br>Distribution within Sesaco<br>for 15$^{th}$ leaf based on stable<br>lines in the crossing program<br>in 2001 (Total number of<br>samples tested = 59)<br>low = 1.2 cm   high = 33.0 cm<br>1 = <7.6 cm; 94.9%<br>2 = <13.9 cm; 3.4%<br>3 = <20.3 cm; 0%<br>4 = <26.6 cm; 0%<br>5 = >26.5 cm; 1.7%<br>avg. = 3.6 cm, std = 4.1 | |
| (15) PETIOLE<br>LENGTH<br>The length of the petiole<br>from the base of the<br>petiole to the start of the<br>leaf blade at the 5$^{th}$, 10$^{th}$,<br>and 15$^{th}$ nodes | Unit of measure: cm<br>Values: average of 3 plants<br>S26 = 13.2 cm for 5$^{th}$ node<br>in 2001 in San Angelo<br>nursery; 6.0 cm for 10$^{th}$<br>node in 2001 in San Angelo<br>nursery; 4.2 cm for 15$^{th}$<br>node in 2001 in San Angelo<br>nursery<br>Distribution within Sesaco<br>for 5$^{th}$ leaf based on stable<br>lines in the crossing program<br>in 2001 (Total number of<br>samples tested = 100)<br>low = 3.7 cm<br>high = 27.5 cm<br>1 = <8.4 cm; 40%<br>2 = <13.2 cm; 47%<br>3 = <18.0 cm; 10%<br>4 = <22.7 cm; 2%<br>5 = >22.6 cm; 1%<br>avg. = 9.7 cm, std = 3.6<br>Distribution within Sesaco<br>for 10$^{th}$ leaf based on stable<br>lines in the crossing program<br>in 2001 (Total number of<br>samples tested = 100)<br>low = 1.4 cm<br>high = 28.5 cm<br>1 = <6.8 cm; 77%<br>2 = <12.2 cm; 20%<br>3 = <17.7 cm; 1%<br>4 = <23.1 cm; 1%<br>5 = >23.0 cm; 1%<br>avg. = 5.7 cm, std = 3.4<br>Distribution within Sesaco<br>for 15$^{th}$ leaf based on stable<br>lines in the crossing program<br>in 2001 (Total number of<br>samples tested = 59)<br>low = 1.4 cm<br>high = 20.0 cm<br>1 = <5.1 cm; 83.1%<br>2 = <8.8 cm; 13.6%<br>3 = <12.6 cm; 1.7%<br>4 = <16.3 cm; 0%<br>5 = >16.2 cm; 1.7%<br>avg. = 4.0 cm, std = 2.8 | See Leaf Blade Length (Character No. 13)<br>on how to collect leaves. In some leaves, the<br>blade on one side of the petiole starts before<br>the other side. This measure should end where<br>the earliest blade starts. There are leaves that<br>have enations where a blade starts and then<br>stops. The enations are not considered part of<br>the leaf blade because they are very irregular<br>from plant to plant and within a plant and<br>should be measured as part of the petiole.<br>Comments: see Leaf Length (Character No.<br>12) for effects of environment<br>The largest leaves are on photosensitive<br>lines which when planted in the tropics fall into<br>the 2$^{nd}$ and 3$^{rd}$ class |
| (16) NUMBER OF<br>CARPELS PER<br>CAPSULE<br>The predominant number<br>of carpels per capsule in<br>the middle half of the<br>capsule zone | Unit of measure: Actual<br>number<br>Values:<br>2 = bicarpellate<br>3 = tricarpellate<br>4 = quadricarpellate<br>S26 = 2 for all crops in all<br>nurseries<br>Distribution within Sesaco<br>based on the introductions<br>received in 1982–2001<br>(Total number of samples<br>tested = 2702)<br>2 = 97.6% | The rating can be taken from about 60 days<br>after planting to all the way to the end of the<br>crop.<br>There are many plants with mixed number<br>of carpels as follows:<br>1. Some bicarpellate plants will have one or<br>more nodes near the center of the capsule zone<br>that have tri- and/or quadricarpellate capsules<br>and vice versa.<br>2. Most tri- and quadri-carpellate plants will<br>begin and end with bicarpellate nodes.<br>3. Some plants have only one carpel that<br>develops. These capsules are generally bent,<br>but on examination the 2$^{nd}$ carpel can be seen. |

TABLE I-continued

Characters Distinguishing the S26 Line

| Character | Rating | Methodology |
|---|---|---|
| | 3 = 0.0004%<br>4 = 2.3%<br>Sesaco has not developed lines with more than 2 carpels. | 4. On all types, flowers may coalesce and double or triple the number of carpels. |
| (17) CAPSULE LENGTH FROM 10cap TEST<br>The length of the capsule from the bottom of the seed chamber to the top of the seed chamber from the outside of the capsule. The tip of the capsule is not included in the measurement. | Unit of measure: cm<br>Values: taken on the median capsule in a 10 capsule sample<br>S26 = 2.2 cm in 2000 in Uvalde nursery; and 2.3 cm in 2001 in Uvalde nursery<br>Distribution within Sesaco based on 10cap test in all nurseries in 1997–2001<br>(Total number of samples tested = 3145)<br>low = 1.3 cm<br>high = 4.5 cm<br>1 = <1.94 cm; 3.6%<br>2 = <2.58 cm; 67.4%<br>3 = <3.22 cm; 27.1%<br>4 = <3.86 cm; 1.7%<br>5 = >3.85 cm; 0.3%<br>avg. = 2.42 cm, std = 0.34 | After the plants are physiologically mature, take 2 capsules from five plants from the middle of the capsule zone. On three capsule per leaf axil lines, one central capsule and one axillary capsule should be taken from the same leaf axil. The measurement is taken on the median capsule of single capsule lines and on the median central capsule on three capsule lines. The measurement is taken on dry capsules because the length can shorten as much as one mm on drydown.<br>The 10 capsules can be sampled from physiological maturity through complete drydown without an effect on this character. Generally, the capsules in the middle of the capsule zone are the longest on the plant.<br>Comments: the length of the capsule is dependent on the amount of moisture, fertility, and population. Higher moisture and fertility increase the length. Higher population decreases the length even with adequate moisture/fertility. |
| (18) SEED WEIGHT PER CAPSULE FROM 10cap TEST<br>The weight of the seed in a capsule from the center of the capsule zone | Unit of measure: grams<br>Values: average of 10 capsules<br>S26 = 0.216 g in 2000 in Uvalde nursery; and 0.252 g in 2001 in Uvalde nursery<br>Distribution within Sesaco based on 10cap test in all nurseries in 1997–2001<br>(Total number of samples tested = 3208)<br>low = 0.053 g<br>high = 0.476 g<br>1 = <0.138 g; 2.7%<br>2 = <0.222 g; 51.1%<br>3 = <0.307 g; 44.9%<br>4 = <0.391 g; 1.2%<br>5 = >0.390 g; 0.1%<br>avg. = 0.216 g, std = 0.043 | See Capsule Length from 10cap Test (Character No. 17) for collection of capsules. The capsules should be dried, the seed threshed out, and the seed weighed.<br>The 10 capsules can be sampled from physiological maturity through complete drydown without an effect on this character. After drydown, only capsules with all their seed are taken. Thus, this test cannot be done on shattering lines after drydown.<br>Generally, the capsules in the middle of the capsule zone have the highest seed weight per capsule on the plant.<br>Comments: see Capsule Length from 10cap Test (Character No. 17) for the effects of environmental factors. |
| (19) CAPSULE WEIGHT PER CAPSULE FROM 10cap TEST<br>The weight of the capsule from the center of the capsule zone after the seed has been removed | Unit of measure: grams<br>Values: average of 10 capsules<br>S26 = 0.113 g in 2000 in Uvalde nursery; and 0.169 g in 2001 in Uvalde nursery<br>Distribution within Sesaco based on 10cap test in all nurseries in 1997–2001<br>(Total number of samples tested = 3207)<br>low = 0.059 g<br>high = 0.395 g<br>1 = <0.126 g; 28.2%<br>2 = <0.193 g; 61.6%<br>3 = <0.261 g; 9.0%<br>4 = <0.328 g; 0.8%<br>5 = >0.327 g; 0.3%<br>avg. = 0.149 g, std = 0.038 | See Capsule Length from 10cap Test (Character No. 17) for collection of capsules. The capsules should be dried, the seed threshed out, and the capsules weighed.<br>The 10 capsules can be sampled from physiological maturity through complete drydown without an effect on this character. Generally, the capsules in the middle of the capsule zone have the highest capsule weight per capsule on the plant.<br>Comments: see Capsule Length from 10cap Test (Character No. 17) for the effects of environmental factors. |
| (20) CAPSULE WEIGHT PER CM OF CAPSULE<br>The weight of a capsule per cm of capsule from the center of the capsule zone | Unit of measure: grams<br>Values: average of 10 capsules<br>S26 = 0.055 g in 2000 in Uvalde nursery; and 0.073 g in 2001 in Uvalde nursery<br>Distribution within Sesaco based on 10cap test in all nurseries in 1997–2001<br>(Total number of samples | The weight is derived by dividing the Capsule Weight per Capsule from 10cap Test (Character No. 19) by the Capsule Length from 10cap Test (Character No. 17).<br>The 10 capsules can be sampled from physiological maturity through complete drydown without an effect on this character.<br>Comments: this character is used instead of capsule width. Capsule width is difficult to measure because there are so many variables in |

TABLE I-continued

Characters Distinguishing the S26 Line

| Character | Rating | Methodology |
|---|---|---|
| | tested = 3144)<br>low = 0.027 g<br>high = 0.123 g<br>1 = <0.046 g; 11.5%<br>2 = <0.065 g; 47.6%<br>3 = <0.085 g; 35.6%<br>4 = <0.104 g; 4.8%<br>5 = >0.103 g; 0.5%<br>avg. = 0.062 g, std = 0.014 | a capsule. In a bicarpellate capsule, the width differs when measuring across one carpel or both carpels. Capsules can also vary through the length of the capsule by being substantially narrower at the bottom, middle or top of the capsule. In 1997, four widths were measured on each capsule and then averaged. This average had a very high correlation to the capsule weight per cm of capsule.<br>See Capsule Length from 10cap Test (Character No. 17) for effects of environmental factors |
| (21) VISUAL SEED RETENTION<br>Amount of seed in most of the capsules in the middle half of the capsule zone when the plant(s) are dry enough for direct harvest with a combine | Subjective rating<br>Values:<br>Seed Retention<br>8 = 100%<br>6 = 75%<br>4 = 50%<br>2 = 25%<br>0 = 0%<br>Intermediate values can be used.<br>V = >74% seed retention (sufficient seed retention for 10cap testing)<br>X = <75% seed retention (unsuitable for direct harvest)<br>W = >74% seed retention on weathering in field after rains and/or winds for more than 3 weeks following complete drydown<br>S26 = W for all crops in all nurseries | When the plants in a plot are dry below where the cutter bar would hit the plant, assign a rating based on the following guidelines. If just identifying lines for further testing, use V/X/W ratings. If identifying lines to use in a crossing program to improve seed retention, use 0–8 ratings. Ratings 6–8 can be seen without removing the capsule from the plant. For the other ratings, the capsules must be opened. Rating is an overall subjective number since retention can vary from plant to plant and even within a plant.<br>The effects of the environment are not fully known. There are indications that in drought or very low fertility conditions, there is less seed retention. When high propulations lead to low moisture or fertility, there is less seed retention. From normal conditions through high moisture/fertility conditions, there does not appear to be an appreciable difference. |
| (22) SHAKER SHATTER RESISTANCE FROM 10cap TEST<br>The amount of seed retention after the capsules are dry, inverted, and put through a shaker | Unit of measure: Actual Number expressed as percentage<br>Values: average of 10 capsules<br>S26 = 72% in 2000 in Uvalde nursery; 74% in 2001 in Uvalde nursery<br>Distribution within Sesaco based on 10cap test in all nurseries in 1997–2001<br>(Total number of samples tested = 3043)<br>low = 0<br>high = 100<br>1 = <20; 12.3%<br>2 = <40; 9.1%<br>3 = <60; 25.1%<br>4 = <80; 44.8%<br>5 = >79.9; 8.8%<br>avg. = 55.2%, std = 23.5 | See Capsule Length from 10cap Test (Character No. 17) for collection of capsules. The capsules should be dried. The capsules should then be placed in flasks on a reciprocal shaker with a 3.8 cm stroke with 250 strokes/min for 10 minutes (see U.S. Pat. No. 6,100,452). The seed that comes out of the capsules should be weighed as 'out seed.' The retained seed should be threshed out of the capsules and weighed to compute the 'total seed'. The shaker shatter resistance is computed as a percentage as follows: (total seed-out seed)/total seed.<br>The 10 capsules can be sampled from physiological maturity through complete drydown without an effect on this character for shatter resistant types. When taking capsules after drydown, only capsules with all their seed are taken. Thus, this test cannot be done on shattering lines after drydown.<br>Comments: there are indications that in drought or very low fertility condition, there is less seed retention. When high populations lead to low moisture or fertility, there is less seed retention. From normal conditions through high moisture/fertility conditions, there does not appear to be an appreciable difference in seed retention. Lines with shaker shatter resistance >64.9% are known as non-dehiscent lines (see U.S. Pat. No. 6,100,452). |
| (23) CAPSULE SHATTERING TYPE<br>Amount of seed retention in a line or plant | Subjective rating<br>Values:<br>SUS = Super-shattering (<2 visual seed retention-equates to <25%)<br>SHA = Shattering (<4 visual seed retention-equates to <50%)<br>SSH = Semi-shattering (4–6 visual seed retention-equates to 50 to 75%) | The rating is based on visual seed retention and other visual observations. The plants remain standing in the field without shocking. GS plants can be identified while the plant is putting on capsules or at drydown because the carpels in the capsules do not form false membranes. There are plants that will have capsules with false membranes on the lower and upper nodes but most of the capsules show no false membranes.<br>ID plants can be identified during the |

TABLE I-continued

Characters Distinguishing the S26 Line

| Character | Rating | Methodology |
|---|---|---|
| | SR = Shatter resistant (>6 visual seed retention without id or gs alleles-equates to >75%)<br>ID = Indehiscent (presence of id/id with capsule closed)<br>IDO = Indehiscent (presence of id/id with capsule open at tip)<br>GS = Seamless (presence of gs/gs with capsule closed)<br>GSO = Seamless (presence of gs/gs with capsule open at tip)<br>S26 = SR in all crops in all nurseries | growing season in that they have enations on the bottoms of the leaves. At dry down they are more difficult to distinguish from other lines that have closed capsules (other than GS). There is less of a suture than other capsule types.<br>SUS, SHA, SSH, and SR are defined by Visual Seed Retention (Character No. 21). Comments: most environmental factors do not have much of an effect on capsule shattering type other than to make it more difficult to distinguish in the overlap zone. Generally, higher moisture, higher fertility, and lower populations will increase the shattering a small amount-less than 10%. The wind can have a large effect in decreasing the amount of seed retention. Rain, dew and fog can also reduce seed retention. |
| (24) NON-DEHISCENT TEST<br>A line that has passed the non-dehiscent test of having shaker shatter resistance >64.9%. ND lines should not have id or gs alleles. | Rating Values:<br>ND = Non-dehiscent line<br>XX = Line that does not pass the non-dehiscent test<br>S26 = ND for all crops in all nurseries<br>Distribution within Sesaco based on 10cap test in all nurseries in 1997–2001<br>(Total number of samples tested = 3031)<br>ND = 56.8%<br>XX = 43.2% | Lines are designated as ND only after they have undergone a minimum of 3 shaker shatter resistance tests. In order to be considered an ND variety, the line must pass the ND threshold in multiple nurseries for multiple years. For example, S26 has a mean of 72.8% seed retention in 87 shaker shatter resistance tests for 1997–2001. |
| (25) DAYS TO FLOWERING<br>Number of days from planting until 50% of the plants are flowering | Unit of measure: days<br>Values: number of days<br>S26 = 41 days in 2000 in Uvalde nursery; and 40 days in 2001 in Uvalde nursery<br>Distribution within Sesaco based on lines in Uvalde nursery in 2000–2001<br>(Total number of samples tested = 1831)<br>low = 33 days<br>high = 89 days<br>1 = <44.2 days; 87.9%<br>2 = <55.4 days; 7.8%<br>3 = <66.6 days; 2.4%<br>4 = <77.8 days; 1.7%<br>5 = >77.7 days; 0.2%<br>avg. = 40.9 days, std = 6.3 | This data is taken as a date and later converted to number of days. Flowering is defined as flowers that are open-not buds. This is a somewhat subjective unit of measure because there is little difference in the appearance of a line that has 40% and a line that has 60% of plants with flowers. In addition, the plots are not walked every day, and thus there is an estimate that the plot was 50% a few days before or after the date of data collection.<br>Comments: flowering can be accelerated by drought and it can be delayed by higher moisture and/or fertility. Higher heat units will decrease the days to flowering.<br>Some lines are photosensitive and will only begin flowering at a certain number of hours of daylight.<br>Start of flowering does not always equate to start of capsule formation. Many lines will flower and not set capsules from the first flowers. |
| (26) DAYS TO FLOWER TERMINATION<br>Number of days from planting until 90% of the plants have stopped flowering | Unit of measure: days<br>Values: number of days<br>S26 = 79 days in 2000 in Uvalde nursery; and 72 days in 2001 in Uvalde nursery<br>Distribution within Sesaco based on lines in Uvalde nursery in 2000–2001<br>(Total number of samples tested = 2668)<br>low = 61 days<br>high = 114 days<br>1 = <71.6 days; 21.1%<br>2 = <82.2 days; 61.5%<br>3 = <92.8 days; 15.9%<br>4 = <103.4 days; 0.8%<br>5 = >103.3 days; 0.8%<br>avg. = 77.1 days, std = 6.9 | This data is taken as a date and later converted to number of days. Flowering is defined as flowers that are open-not buds. At the end of the flowering period, the rate that a plant puts on open flowers is reduced. Thus, there can be more than 10% of plants with buds and still have reached this measure since there will not be more than 10% flowering any one day.<br>This is a somewhat subjective unit of measure because there is little difference in the appearance of a line that has 85% and a line that has 95% of plants with no flowers. In addition, the plots are not walked every day, and thus there is an estimate that the plot was 90% a few days before or after the date of data collection. Another problem is that under low moisture conditions the plots can reach the 90% mark only to begin flowering again after a rain. In those cases the data is adjusted to the later number of days. |

TABLE I-continued

Characters Distinguishing the S26 Line

| Character | Rating | Methodology |
|---|---|---|
| | | The measure is based on the number of plants and not the number of flowering heads. The branches will stop flowering before the main stem, and thus the plot will appear like there are more plants not flowering. Comments: flower termination can be accelerated by lower moisture and/or fertility, and it can be delayed by higher moisture and/or fertility. Higher heat units will decrease the Days to Flower Termination. It is known that there are lines that stop flowering sooner than expected in northern latitudes, but it is not known if this is due to shorter photoperiod or cool temperatures. |
| (27) DAYS TO PHYSIOLOGICAL MATURITY Number of days from planting until 50% of the plants reach physiological maturity | Unit of measure: days Values: number of days S26 = 96 days in 2000 in Uvalde nursery; and 103 days in 2001 in Uvalde nursery Distribution within Sesaco based on lines in Uvalde nursery in 2000–2001 (Total number of samples tested = 2374) low = 77 days high = 140 days 1 = <89.6 days; 16.8% 2 = 102.2 days; 58.0% 3 = <114.8 days; 23.6% 4 = <127.4 days; 1.4% 5 = >127.3 days; 0.2% avg. = 97.1 days, std = 7.1 | This data is taken as a date and later converted to number of days. Physiological maturity (PM) is defined as the point at which ¾ of the capsules have seed with final color. In most lines, the seed will also have a seed line and tip that are dark. This is a somewhat subjective unit of measure because there is little difference in the appearance of a line that has 40% and a line that has 60% of plants with PM. In addition, the plots are not walked every day, and thus there is an estimate that the plot was 50% a few days before or after the date of data collection. Comments: The concept of physiological maturity in sesame was developed by M.L. Kinman (personal communication) based on the concept of determining the optimum time to cut a plant and still harvest 95–99% of the potential yield. When the seed has final color, the seed can germinate under the proper conditions. If the plant is cut at physiological maturity, most of the seed above the ¾ mark will continue maturing enough for germination, but will not have as much seed weight. Since in even a fully mature plant, there is less seed weight made at the top of the plant, this loss of seed weight does not seriously affect the potential seed weight of the plant. Although present harvest methods let the plants mature and go to complete drydown, PM is important because after that point, the crop is less susceptible to yield loss due to frost or disease. The PM is also important if the crop is to be swathed or dessicants are to be applied. Physiological maturity can be accelerated by lower moisture and/or fertility, and it can be delayed by higher moisture and/or fertility. Higher heat units will decrease the days to physiological maturity. Cool weather can delay physiological maturity. |
| (28) SEED COLOR The color of the seed coat | Subjective rating Values: WH = White BF = Buff TN = Tan LBR = Light brown GO = Gold LGR = Light gray GR = Gray BR = Brown RBR = Reddish brown BL = Black S26 = BF in all crops in all nurseries Distribution within Sesaco based on seed harvested in all nurseries in 1982–2001 (Total number of samples tested = 161,809) WH = 0.8% BF = 74.8% | This data is taken in the laboratory with the same lighting for all samples. The seed from the whole plant is used. Seed coat color is taken on mature seeds. If there is any abnormal termination, the colors are not quite as even. The color of immature seed varies. Usually light seeded lines have tan to light brown immature seed; tan, light brown, gold, brown light gray, and gray lines have lighter immature seed; black lines can have tan, brown, or gray immature seed. Usually, moisture, fertility, population and light intensity do not have an effect on seed coat color. Light colored seeds in a drought may have a yellowish tinge. Seeds in some lines in the tan, light brown and gold range can change from year to year among themselves. |

TABLE I-continued

Characters Distinguishing the S26 Line

| Character | Rating | Methodology |
|---|---|---|
| | TN = 9.0%<br>LBR = 1.4%<br>GO = 1.5%<br>LGR = 0.6%<br>GR = 1.4%<br>BR = 6.5%<br>RBR = 0.6%<br>BL = 3.5% | |
| (29) SEED WEIGHT-100 SEEDS FROM WHOLE PLANT<br>Weight of 100 seeds taken from the whole plant | Unit of measure: grams<br>Values: average of 3 samples<br>S26 = 0.30 g in 2000 in Uvalde nursery; and 0.31 g in 2001 in Uvalde nursery<br>Distribution within Sesaco based on stable lines in all nurseries in 1997–2001<br>(Total number of samples tested = 1984)<br>low = 0.10 g<br>high = 0.46 g<br>1 = <0.172 g; 0.6%<br>2 = <0.244 g; 10.1%<br>3 = <0.316 g; 56.0%<br>4 = <0.388 g; 26.1%<br>5 = >0.387 g; 7.3%<br>avg. = 0.306 g, std = 0.05 | Count out 100 seeds and weigh. The seed must be dry.<br>Comments: the weight increases with higher moisture/fertility. Generally, the weight is lighter than the seed weight taken from the 10cap test. |
| (30) UVALDE KILL RESISTANCE<br>The amount of plants killed by root rots in the Sesaco nurseries in Uvalde, TX | Subjective rating<br>Values: ratings are based on the number of plants killed in a plot. Before physiological maturity (PM), the following ratings are used:<br>1 = >90% kill before Days to Flowering Termination (Character No. 26)<br>2 = >90% kill between Days to Flowering Termination (Character No. 26) and Days to Physiological Maturity (Character No. 27)<br>After PM, the following ratings are used:<br>3 = >90% kill<br>4 = 50 to 89% kill<br>5 = 25 to 49% kill<br>6 = 10 to 24% kill<br>7 = less than 10% kill<br>8 = no kill<br>S26 = 5.60 in 2000 in Uvalde nursery; and 7.22 in 2001 in Uvalde nursery<br>Distribution within Sesaco based on lines in Uvalde nursery in 2000–2001<br>(Total number of samples tested = 3045)<br>low = 1.00<br>high = 8.00<br>1 = <1.6; 1.7%<br>2 = <3.2; 16.7%<br>3 = <4.8; 38.7%<br>4 = <6.4; 31.2%<br>5 = >6.3; 11.6%<br>avg. = 4.52, std = 1.49 | On the week a plot reaches PM, a rating is assigned. The ratings are then taken for 2 additional weeks. The three ratings are averaged for a final kill rating. For example, if a plot has a final kill of 766, the average for the plot will be 6.33. When a value of 1 or 2 is assigned, there are no additional ratings and there is no averaging.<br>There are three root diseases that affect sesame in Texas: *Fusarium oxysporum*, *Macrophomina phaseoli*, and *Phytophtora parasitica*. Between 1988 and the present, spores of these three have been accumulated in one small area of Uvalde, and thus it is an excellent screening area for the diseases. Although each root rot attacks sesame in a different way with different symptoms, no effort is made to differentiate which disease is the culprit in each plot. Pathological screenings in the past have found all 3 pathogens present in dead plants.<br>Comments: normally, the ratings will decrease a maximum of one value per week. There is an overlap between any two ratings, but this is overcome to a certain extent by using three ratings over 2 weeks.<br>The amount of kill is usually increased with any type of stress to the plants. Drought can increase the amount of Macrophomina; too much water can increase the amount of Phytophtora; high temperatures and humidity can increase the amount of Fusarium and Phytophtora. High population can increase all three diseases.<br>The ratings for any one year can be used to compare lines grown in that year, but should not be used to compare lines grown in different years. The amount of disease in any one year is highly dependent on moisture, humidity, and temperatures. |
| (31) RESISTANCE TO FUSARIUM WILT<br>(*F. oxysporum*)<br>Amount of resistance to Fusarium wilt | Subjective rating<br>Values: 0 to 8 scale<br>% of infected plants<br>8 = Zero disease<br>7 = <10% infected<br>4 = 50% infected<br>1 = >90% infected<br>0 = all infected<br>NT = not tested | Ratings can be done in several ways:<br>1. Take ratings after the disease is no longer increasing<br>2. Take ratings on consecutive weeks until disease is no longer increasing and average ratings.<br>3. Take periodic ratings and average ratings.<br>Comments: Fusarium has been a problem in South Texas, particularly on fields that have |

TABLE I-continued

Characters Distinguishing the S26 Line

| Character | Rating | Methodology |
|---|---|---|
| | NEC = no economic damage-not enough disease to do ratings S26 = 7 in 1998–2001 in Uvalde nursery | been planted with sesame before. Normally, only the Uvalde Kill Resistance (Character No. 30) rating is taken. |
| (32) RESISTANCE TO PHYTOPHTORA STEM ROT (*P. parasitica*) Amount of resistance to Phytophtora stem rot | Subjective rating See Values for Fusarium S26 = NT | See Methodology for Resistance to Fusarium Wilt (Character No. 31) Comments: Phytophtora has been a problem in Arizona and Texas, particularly on fields that have been over-irrigated. Normally, only the Uvalde Kill Resistance (Character No. 30) rating is taken. |
| (33) RESISTANCE TO CHARCOAL ROT (*Macrophomina phaseoli*) Amount of resistance to Charcoal rot | Subjective rating See Values for Fusarium S26 = NT | See Methodology for Resistance to Fusarium Wilt (Character No. 31) Comments: Macrophomina has been a problem in Arizona and Texas, particularly on fields that go into a drought. Normally, only the Uvalde Kill Resistance (Character No. 30) rating is taken. |
| (34) RESISTANCE TO BACTERIAL BLACK ROT (*Pseudomonas sesami*) Amount of resistance to bacterial black rot | Subjective rating See Values for Fusarium S26 = NT | See Methodology for Resistance to Fusarium Wilt (Character No. 31) Comments: this disease occurs occasionally when there is continual rainy weather with few clouds. In most years, the disease abates once the weather changes. No economic damage has been noticed. |
| (35) RESISTANCE TO SILVERLEAF WHITE FLY (*Bemisia argentifolii*) Amount of resistance to the silverleaf white fly | Subjective rating Values: 0 to 8 scale 8 = Zero insects 7 = Few insects 4 = Many insects 1 = Insects killing the plants NT = not tested NEC = no economic damage-not enough insects to do ratings S26 = NEC in 2000 in Uvalde nursery | Ratings can be done in several ways: 1. Take ratings after the insects are no longer increasing. 2. Take ratings on consecutive weeks until insects are no longer increasing and average ratings. 3. Take periodic ratings and average ratings. Comments: there have been very few years (1991–1995) where the incidence of silverleaf white fly has affected nurseries or commercial crops. In most years, a few white flies can be seen in the sesame with no economic damage. In the middle 1990s, the USDA began introducing natural predators of the silverleaf white fly in the Uvalde area. It is not known if the predators reduced the effects of the white fly or there is a natural tolerance to white fly in the current varieties. In the 2000 nursery, some lines were killed by the white fly. Higher temperatures decrease the number of days between generations. There are indications that higher moisture and fertility increase the incidence of white flies, but there is no definitive data. The sweet potato white fly (*Bemisia tabaci*) has been observed in nurseries since 1978 without any economic damage. |
| (36) RESISTANCE TO GREEN PEACH APHIDS (*Myzus persicae*) Amount of resistance to the green peach aphid | Subjective rating See Values for White Fly S26 = NEC in 2000 in Uvalde nursery | See Methodology for Resistance to Silverleaf White Fly (Character No. 35) Comments: there have been very few years (1990–1995) where the incidence of green peach aphid has affected nurseries or commercial crops. In most years, a few aphids can be seen in the sesame with no economic damage. There have been many years in West Texas when the cotton aphid has decimated the cotton and did not build up on adjacent sesame fields. Higher moisture and fertility increase the susceptibility to aphids. |
| (37) RESISTANCE TO POD BORERS (Heliothis spp.) Amount of resistance to pod borers | Subjective rating See Values for White Fly S26 = NEC in 2001 in Uvalde nursery | See Methodology for Resistance to Silverleaf White Fly (Character No. 35) Comments: there have been very few years (1985) where the incidence of Heliothis has affected nurseries or commercial crops. In most years, a few borers can be seen in the sesame with no economic damage. |
| (38) RESISTANCE TO ARMY WORMS | Subjective rating See Values for White Fly | See Methodology for Resistance to Silverleaf White Fly (Character No. 35) |

TABLE I-continued

Characters Distinguishing the S26 Line

| Character | Rating | Methodology |
|---|---|---|
| (Spodoptera spp.) Amount of resistance to army worms | S26 = NT | Comments: there have been very few years (1984–1987) where the incidence of Spodoptera has affected commercial crops in Arizona. In Texas, army worms have decimated cotton and alfalfa fields next to sesame without any damage to the sesame. It is not known if the Arizona army worm is different from the Texas army worm. |
| (39) RESISTANCE TO CABBAGE LOOPERS (*Pieris rapae*) Amount of resistance to cabbage loopers | Subjective rating See Values for White Fly S26 = NT | See Methodology for Resistance to Silverleaf White Fly (Character No. 35) Comments: there have been very few years (1992–1993) where the incidence of cabbage loopers has affected nurseries. In commercial sesame, cabbage loopers have been observed with no economic damage. |

[a]Uvalde nursery as described above.
[b]San Angelo nursery as described above.

In developing sesame varieties for the United States, there are four major characters that are critical: *Shaker Shatter Resistance* (Character No. 22), *Uvalde Kill Resistance* (Character No. 30), *Days to Physiological Maturity* (Character No. 27), and *Seed Weight—100 Seeds from Whole Plant* (Character No. 29). The first three characters contribute to yield which is the ultimate determinant for the farmer to grow a variety. In improving the characters, the yields have to be comparable to or better than current varieties, or provide a beneficial improvement for a particular geographical or market niche. *Shaker Shatter Resistance* determines how well the plants will retain the seed while they are drying down in adverse weather. *Uvalde Kill Resistance* determines whether the plants can finish their cycle and have the optimum seed fill. *Days to Physiological Maturity* determines how far north and to which elevation the varieties can be grown. *Seed Weight—100 Seeds from Whole Plant* determines the market for the seed. Lack of *Uvalde Kill Resistance* can reduce *Seed Weight—100 Seeds from Whole Plant*. In parts of the United States where there is little rain in dry years *Resistance to Drought* (Character No. 11) becomes important.

There are other characters important in developing commercial sesame varieties explained in Langham, D. R. and T. Wiemers, 2002, "Progress in mechanizing sesame in the US through breeding", In: J. Janick (ed.), *Trends in new crops and new uses*, ASHS Press, Alexandria, Va. *Branching Style* (Character No. 1), *Height of Plant* (Character No. 5) and *Height of First Capsule* (Character No. 6) are important in combining. *Capsule Zone Length* (Character No. 7), *Number of Capsule Nodes* (Character No. 8), *Average Internode Length within Capsule Zone* (Character No. 9), and *Seed Weight per Capsule* (Character No. 18) are important in creating potential *Yield at Drydown* (Character No. 10). Leaf dimensions (Characters No. 12, 13, 14, and 15) are important in determining optimum populations. *Number of Capsules per Leaf Axil* (Character No. 2), *Number of Carpels per Capsule* (Character No. 16), *Capsule Length* (Character No. 17), *Capsule Weight per Capsule* (Character No. 19), and *Capsule Weight per cm of Capsule* (Character No. 20) are important in breeding for *Visual Seed Retention* (Character No. 21) which leads to testing for *Shaker Shatter Resistance* and determining the *Capsule Shattering Type* (Character No. 23). *Days to Flowering* (Character No. 25), *Days to Flower Termination* (Character No. 26), and *Days to Physiological Maturity* (Character No. 27) are highly correlated and important in determining the geographical range for the variety. In the United States and Europe, the *Seed Color* (Character No. 28) is important since the majority of the market requires white or buff seed. There are limited markets for gold and black seed in the Far East. All other colors can only be used in the oil market. In the United States, resistance to diseases and pests (Characters No. 31 to 39) are critical to allow the crop to reach maturity and harvest.

FIG. 2 provides the *Shaker Shatter Resistance* of all the varieties released by Sesaco since 1981. The figures are the mean from all testing in all nurseries from 1997 to 2001. S01 was an indehiscent variety with excellent seed retention, but the seed could not be threshed out without making the seed unmarketable. SO2 through SO, S12, and S14 were developed for swathing at *Days to Physiological Maturity*, drying in windrows, and then picking up with a combine. All of these varieties had good yields when there was little rain and high temperatures at harvest time. In the bad weather, the yields were reduced. Attempts were made to let these varieties dry down standing and then combining, but the yields were not commercially adequate. S11 was the first variety that could be left standing for harvest with adequate yields in normal weather. With the exception of S17, varieties S15 through S22 were released for specific niches. S17 replaced S1 in most locations until it was replaced by S23 and S24. In 2001, S25 replaced S23. S23 is considered to be the minimum acceptable *Shaker Shatter Resistance* for commercial use. S26 provides about 72.8% seed retention which is comparable to S24 and S25 and a desirable amount for mechanized harvesting.

Figure 3:
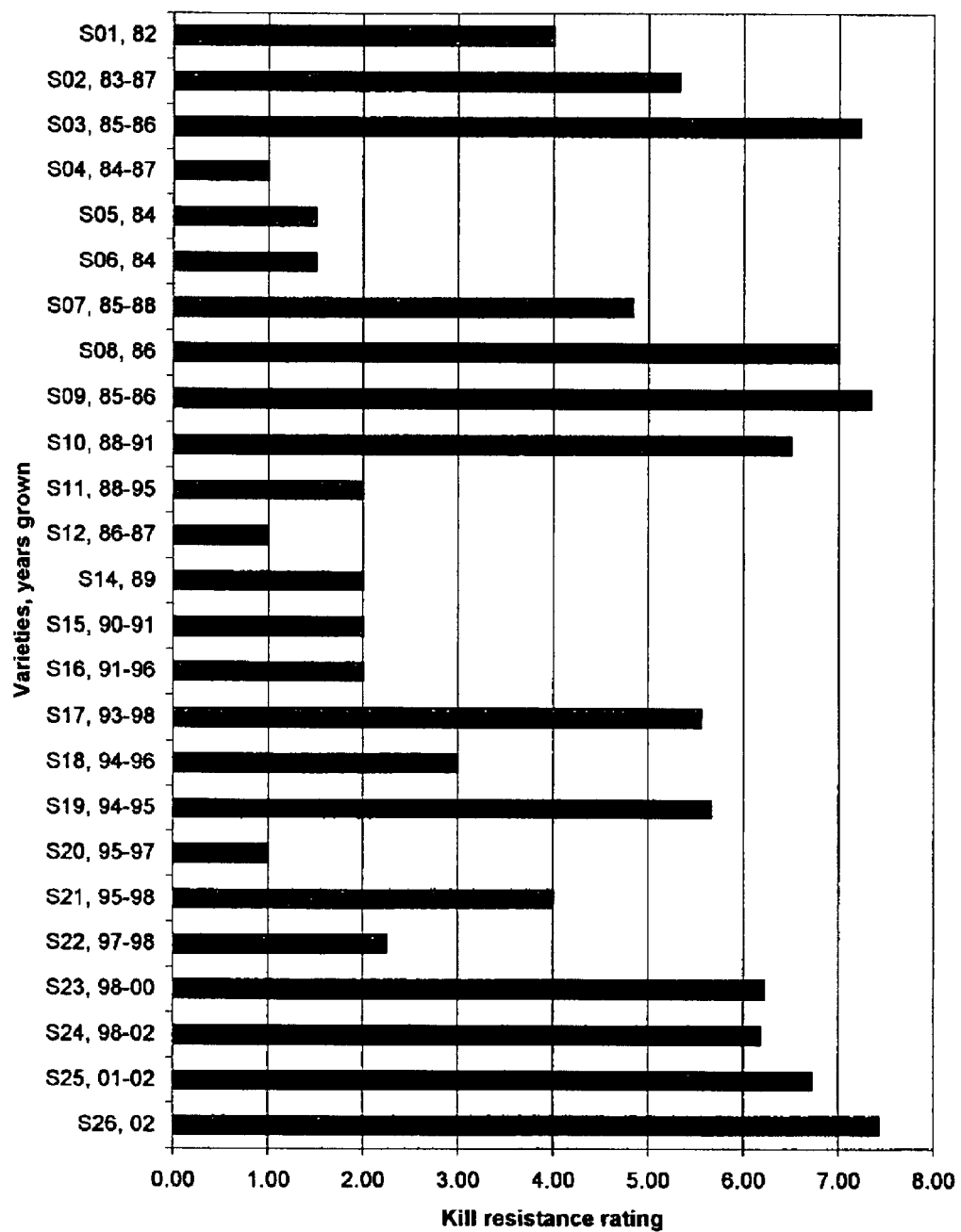
FIG. 3 depicts a comparison of the kill resistance ratings in Uvalde, Tex., in 2001 for the varieties released by Sesaco.

FIG. 3 provides the *Uvalde Kill Resistance* of all the varieties released by Sesaco since 1981 as compared in the Uvalde nursery in 2001 using all plots. *Uvalde Kill Resistance* is a composite rating of resistance to three root rots: Fusarium, Phytophtora, and Macrophomina. When sesame is first introduced into a growing area, there are few disease problems, but over time the spores of these fungi accumulate and disease resistance becomes critical. When sesame was first introduced in Uvalde in 1988, the yields were high. As farmers planted on the same fields in subsequent years, the yields decreased. S11 was very susceptible to these root rots, and thus, it was replaced by S17, which was subsequently replaced by S23 and S24. In 2001, S25 replaced S23. S26 exhibits a rating of 7.42, which is better than previously released non-dehiscent lines.

Figure 4:
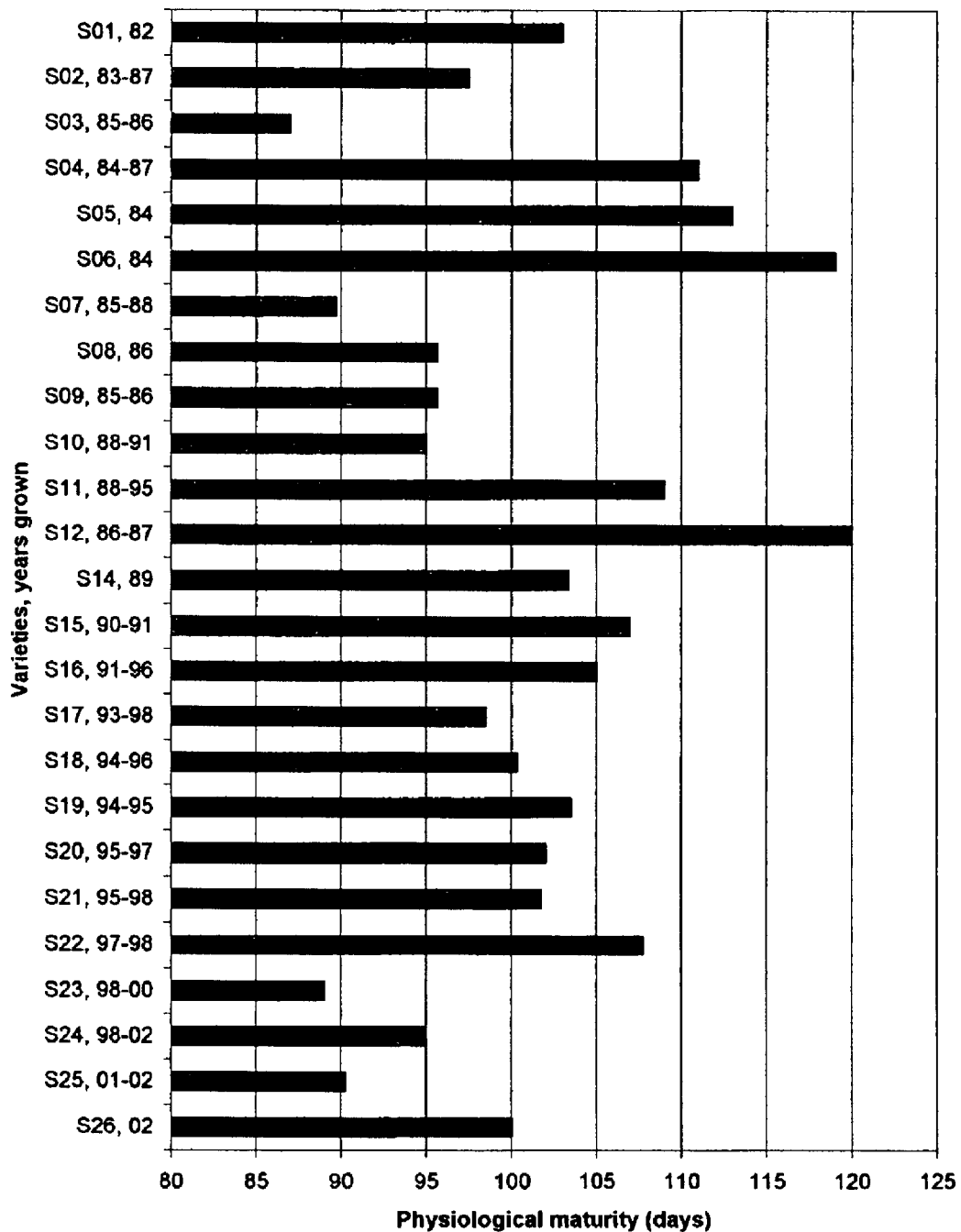
FIG. 4 depicts a comparison of the mean days to physiological maturity from 1998 to 2001 for the varieties released by Sesaco.

FIG. 4 provides the mean *Days to Physiological Maturity* of all the varieties over the past four years in the Uvalde nursery. In the United States, sesame is currently grown from South Texas to southern Kansas. The growing window of a crop is determined by the earliest the crop can be planted in the spring as the ground warms up, and the onset of cold weather in the fall. Current sesame varieties require about 21° C. ground temperature to establish an adequate population. In most years, the ground is warm enough in South Texas in middle April and in southern Kansas in late May. Current sesame varieties require night temperatures above 5° C. for normal termination. In most years, the night temperatures are warm enough in South Texas until middle November and in southern Kansas until middle October. There have been years when cold fronts affect the growth of sesame in the middle of September in the north. East of Lubbock, Tex., the elevations begin climbing towards the Rocky Mountains, and there are later warm temperatures in the spring and earlier cold temperatures in the fall. In all years, if the sesame is planted as early as temperatures allow, lines with *Days to Physiological Maturity* of 105 days or less will have no problems. However, most areas are rainfed, and it is essential to have a planting rain before planting the sesame. Thus, the earlier the *Days to Physiological Maturity* of the variety, the more flexibility the farmers have with planting date. In South Texas, the goal is to have varieties with a *Days to Physiological Maturity* of less than 110 days while in southern Kansas the goal is less than 90 days. The mean *Days to Physiological Maturity* for S26 is 100 days, and thus, S26 is limited in terms of planting date and geographical distribution.

Figure 5:
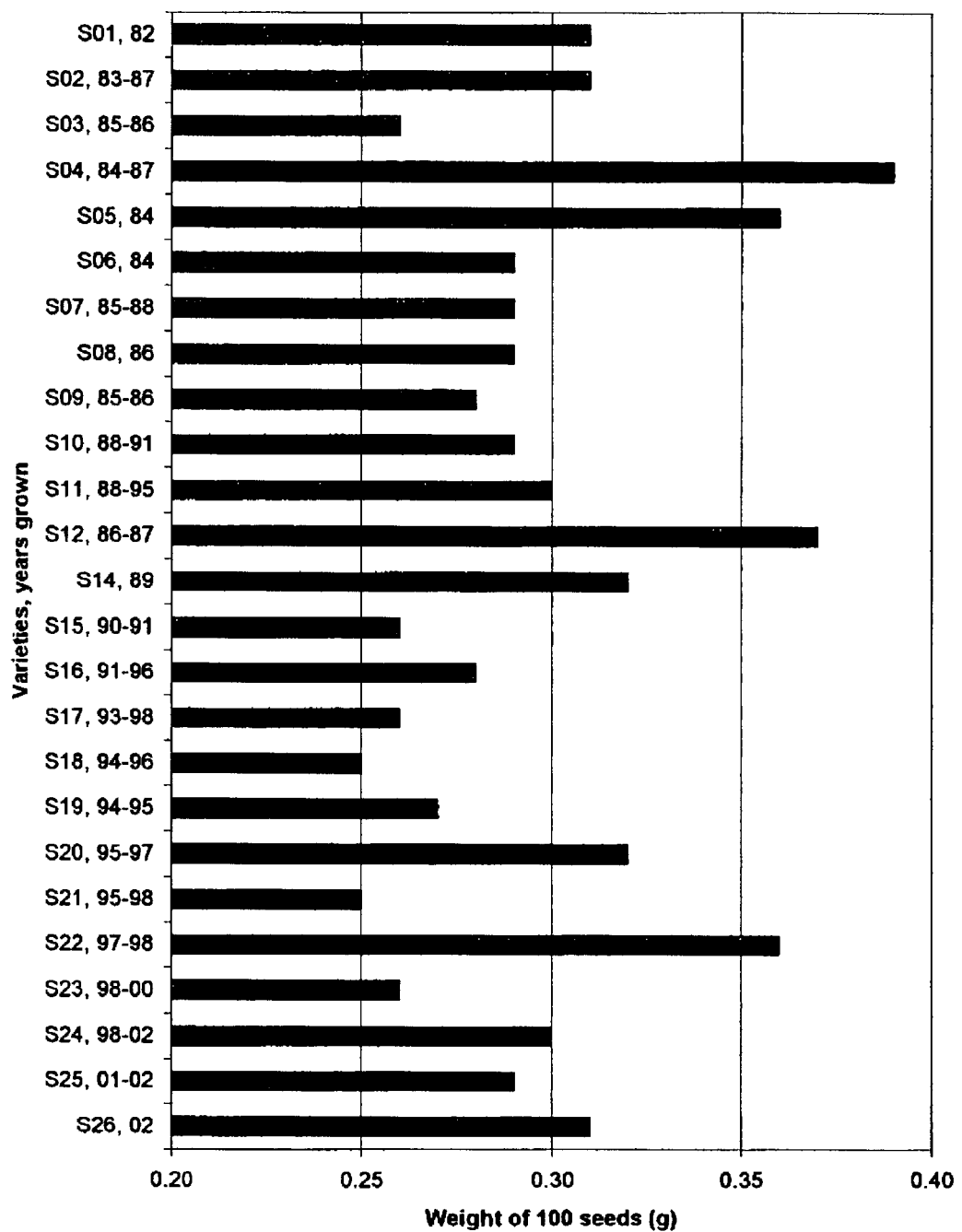
FIG. 5 depicts a comparison of the mean weight of 100 seeds in grams from 1997 to 2001 for the varieties released by Sesaco.

FIG. 5 provides the average *Seed Weight—100 Seeds from Whole Plant* of all varieties between 1997 and 2001. The dehulled market is the premium use of sesame in the United States and Europe. In recent years, dehulled processors have been increasing the specifications of *Seed Weight—100 Seeds from Whole Plant* to between 0.28 and 0.30 g, and larger seed is preferable. To date, the Sesaco varieties with the highest *Seed Weight—100 Seeds from Whole Plant* have had marginal *Shaker Shatter Resistance* and poor *Uvalde Kill Resistance*. Some markets have no specifications on seed weight, but larger seed is still desirable. The mean *Seed Weight—100 Seeds from Whole Plant* for S26 is 0.31 g, which is larger than the current varieties of S24 and S25. The processors prefer the size of S26 for dehulled products on top of breads and buns.

Figure 6:
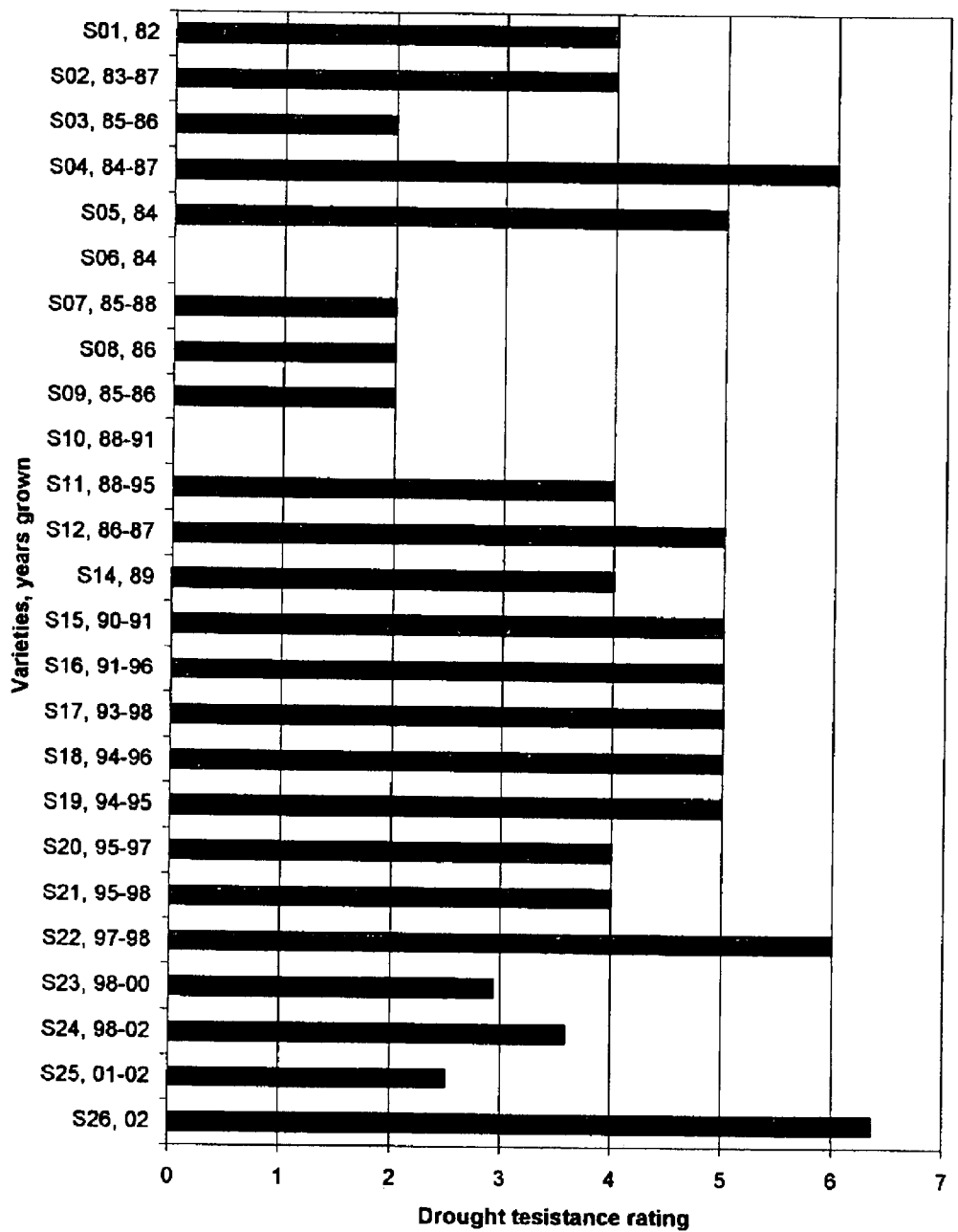
FIG. 6 depicts a comparison of the mean resistance to drought in San Angelo, Tex., in 2000 for the varieties released by Sesaco.

FIG. 6 provides the mean *Resistance to Drought* of all the varieties in the 2000 San Angelo nursery. In 2000, in San Angelo, there was a drought with very low moisture in the soil profile at planting, and the one irrigation of less than 50 mm was applied too late to help the crop. *Resistance to Drought* ratings were taken, and S26 was the best with 6.4. The other two good varieties were SO4 and S22, but these are extremely susceptible to root rots.

Prior to 1988, all of the commercial sesame in the United States was grown in Arizona. S01 through S10, S12, and S14 were specifically developed for Arizona. From 1988 to 1991, there was a transition from Arizona to Texas. In 1996, sesame spread into Oklahoma, and in 1998, into Kansas. In introducing sesame to Texas, the swathing technology was tried on S07 and S10, but farmers did not have the proper equipment; the plants fell into the furrows and could not be picked up; and/or blowing sand covered parts of the windrows. S11 was the first variety that could be combined directly, and S11 persisted until 1995. However, in addition to being susceptible to root rots, S11 was also susceptible to pests such as green peach aphids (*Myzus persicae*) (Character No. 36) and silverleaf white fly (*Bemisia argentifolii*) (Character No. 35), and S11 had too long a *Days to Physiological Maturity* (109 days) for West Texas. S15 was introduced for West Texas, but shorter *Days to Physiological Maturity* (107 days) was still not early enough and the *Shaker Shatter Resistance* (38.7% seed retention) was not adequate. S16 was released specifically because it was tolerant to the white fly, but it did not have good *Shaker Shatter Resistance* (42% seed retention) or Uvalde Kill Resistance (2.0 rating), and it was susceptible to lodging. S17 had better *Uvalde Kill Resistance* (5.56 rating), aphid resistance, and white fly resistance than S11. With an earlier *Days to Physiological Maturity* (98.5 days), S17 was the first variety that was suitable for West Texas and southern Kansas; however, S17 was susceptible to lodging. S18 and S21 were released for flavor for the Japanese organic market. S19 had improved lodging resistance over S17, but the yields in non-windy areas were not as good as S17. S20 and S22 were released because of excellent drought resistance. In the rainfed areas of Central Texas, the yields of S20 and S22 were higher than S17, the large seed was desirable to processors, and no root rots had been seen. However, the root rot spores began accumulating, and the S20 and S22 had to be discontinued. S24 replaced S17 based on higher *Shaker Shatter Resistance* (74.4% for S24 compared to 60.8% for S17), better *Uvalde Kill Resistance* (rating of 6.18 for S24 compared to 5.56 for S17), shorter *Days to Physiological Maturity* (95.0 days for S24 compared to 98.5 for S17), and larger *Seed Weight—100 Seeds from Whole Plant* (0.30 g for S24 compared to 0.26 g for S17). S23 was used in southern Kansas and northern Oklahoma because of a shorter *Days to Physiological Maturity* than S24 (89 days for S23 compared to 95 days for S24), but the *Seed Weight—100 Seeds from Whole Plant* was marginal (0.26 g for S23 compared to 0.30 g for S24). S25 replaced S23 in southern Kansas and northern Oklahoma even though the *Days to Physiological Maturity* is not quite as short (90.25 days for S25 compared to 89.0 days for S23). Compared to S23, S25 has better *Shaker Shatter Resistance* (72.9% seed retention for S25 compared to 65.7% seed retention for S23) and *Uvalde Kill Resistance* (rating of 6.72 for S25 compared to 6.22 for S23), but the major reason for the replacement is the *Seed Weight—100 Seeds from Whole Plant* (0.29 g for S25 compared to 0.26 g for S23).

S26 was developed for its *Resistance to Drought* with a rating of 6.4 as compared to the other two current varieties: 3.6 for S24 and 2.5 for S25. Compared to S24 and S25, S26 has comparable *Shaker Shatter Resistance* (72.8% seed retention for S26 compared to 72.9% for S25 and 74.4% for S24), better *Uvalde Kill Resistance* (rating of 7.42 for S26 compared to 6.72 for S25 and 6.18 for S24), better *Seed Weight—100 Seeds from Whole Plant* (0.31 g for S26 compared to 0.29 g for S25 and 0.30 g for S24). In terms of the *Days to Physiological Maturity* S26 takes longer to mature than the current varieties (100 days for S26 compared to 90.25 days for S25 and 95 days for S24. As a result, there is a limit to the geographical range of S26 to the north.

Over the past 24 years, Sesaco has tested 2,738 introductions from all over the world. Commercial samples have been obtained from China, India, Sudan, Ethiopia, Burkina Faso, Nigeria, Mozambique, Pakistan, Myanmar, Bangladesh, Vietnam, Egypt, Mexico, Guatemala, Nicaragua, Venezuela, Thailand, Turkey, Upper Volta, Uganda, Mali, Kenya, Indonesia, Sri Lanka, Afghanistan, Philippines, Colombia, Ivory Coast, Gambia, Somalia, Eritrea, Paraguay, and El Salvador. Additional research seed has been received from the commercial countries and from many other countries such as Australia, Iraq, Iran, Japan, Russia, Jordan, Yemen, Syria, Morocco, Saudi Arabia, Angola, Argentina, Peru, Brazil, Cambodia, Laos, Sri Lanka, Ghana, Gabon, Greece, Italy, South Korea, Libya, Nepal, Zaire, and Tanzania. Research seed received from one country may have originated from another unspecified country. All the commercial and research introductions have Capsule Shattering Type "SHA". Using selected characters from Table I, Table II provides a character differentiation between S26 and name cultivars from all over the world.

Table III compares S24, S25, and S26 using all of the characters in Table I. In Table III, some of the values are different from the values used in FIGS. 2–5. The values in Table III are from side by side plots grown under the same conditions, and the values in FIG. 2 to FIG. 5 are based on averages of all of the S24, S25, and S26 plots grown in the nurseries and dates indicated. The major differences are indicated in the "Dif" column by a "C" for commercially important differences and an "M" for morphological differences.

TABLE II

Character Differentiation of Various Sesame Varieties[a]

| Character | Rating | Name cultivars tested by Sesaco |
|---|---|---|
| Capsule Shattering Type (Character No. 23) | SHA | From Venezuela: Venezuela 51, Venezuela 52, Guacara, Aceitera, Inamar, Acarigua, Morada, Capsula Larga, Arawaca, Piritu, Glauca, Turen, DV9, Fonucla, UCLA From Mexico: Pachequeno, Yori, Anna, Teras, Denisse, Canasta, Tehvantepeter From India: TMV1, TMV3 From Turkey: Ozberk, Muganli, Gamdibi, Marmara From Israel: DT45 From Guatemala: R198, R30 From Texas: Llano, Margo, Dulce, Blanco, Paloma, Oro, Renner 1 and 2, Early Russian From California: UCR3, UCR4, Eva, Calinda (Cal Beauty) From Thailand: KU18 From Korea: Danback, Gwansan, Pungyiong, Suweon, Yuseong, Hanseon, Ahnsan, Kwangsan, Jinback, Pungsan, Sodan, Yangheuk, Konheuk, Whaheuck, Sungboon |
| | SSH | From Sesaco: S02, S03, S04, S05, S06, S07, S08, S09, S10, S12, S14 |
| | ID | From Venezuela: G2, Morada id From Texas: Rio, Delco, Baco, Improved Baco, Roy, Eli From South Carolina: Palmetto From California: UCR234 From Sesaco: S01 |
| | SR | All others, go to Non-dehiscent Test |
| Non-dehiscent Test (Character No. 24) | XX | From Sesaco: S11, S15, S16, S17, S18, S19, S20, S21 |
| | ND | All others, go to Branching Style |
| Branching Style (Character No. 1) | U | From Sesaco: S22, 19A, 11W |
| | B | All others, go to Number of Capsules per Leaf Axil |
| Number of Capsules per Leaf Axil (Character No. 2) | 3 | From Sesaco: S23 |
| | 1 | From Sesaco: S24, S25, S26 |

[a]SHA = shattering; SSH = semi-shattering; ID = indehiscent; SR = shatter resistant; XX = not non-dehiscent according to the teachings of U.S. Pat. No. 6,100,452; ND = non-dehiscent according to the teachings of U.S. Pat. No. 6,100,452; U = uniculm branching style; and B = true branching.

TABLE III

Character Comparison of S24, S25, and S26[a]

| No. | Character | Year/nursery | S24 | S25 | S26 | Dif |
|---|---|---|---|---|---|---|
| 1 | Branching Style | All | B | B | B | |
| 2 | Number of Capsules per Leaf Axil | All | 1 | 1 | 1 | |
| 3 | Maturity Class | 1998–2001 UV | M | E | M | C |
| 4 | Plant Phenotype | All | B1M | B1E | B1M | C |
| 5 | Height of Plant (cm) | 2000 UV | 126 | 125 | 128 | |
| | | 2001 UV | 129 | 126 | 144 | |
| 6 | Height of First Capsule (cm) | 2000 UV | 50 | 49 | 53 | |
| | | 2001 UV | 45 | 41 | 50 | |
| 7 | Capsule Zone Length (cm) | 2000 UV | 76 | 76 | 75 | |
| | | 2001 UV | 84 | 86 | 94 | |
| 8 | Number of Capsule Nodes | 2000 UV | 27 | 26 | 23 | |
| | | 2001 UV | 29 | 29 | 29 | |
| 9 | Average Internode Length within Capsule Zone (cm) | 2000 UV | 2.8 | 3.0 | 3.3 | M |
| | | 2001 UV | 2.9 | 3.0 | 3.3 | M |
| 10 | Yield at Drydown (kg/ha) | 2000 UV | 1270 | 1343 | 1421 | C |
| | | 2001 UV | 1074 | 1614 | 1696 | C |
| | | 2000 SA | 202 | 87 | 390 | C |
| | | 2001 SA | 1514 | 1450 | 1611 | C |
| 11 | Resistance to Drought | 2000 SA | 3.6 | 2.5 | 6.4 | C |
| 12 | Leaf Length (cm) | 5th- 2001 SA | 19.7 | 22.6 | 30.4 | M |
| | | 10th- 2001 SA | 19.2 | 18.7 | 20.1 | |
| | | 15th- 2001 SA | 15.5 | 14.8 | 18.6 | M |
| 13 | Leaf Blade Length (cm) | 5th- 2001 SA | 14.4 | 14.6 | 17.1 | M |
| | | 10th- 2001 SA | 14.3 | 14.1 | 14.1 | |
| | | 15th- 2001 SA | 12.7 | 12.1 | 14.4 | M |
| 14 | Leaf Blade Width (cm) | 5th- 2001 SA | 9.3 | 8.3 | 19.5 | M |
| | | 10th- 2001 SA | 4.2 | 3.8 | 6.5 | M |
| | | 15th- 2001 SA | 2.7 | 2.3 | 3.2 | M |

TABLE III-continued

Character Comparison of S24, S25, and S26[a]

| No. | Character | Year/nursery | S24 | S25 | S26 | Dif |
|---|---|---|---|---|---|---|
| 15 | Petiole Length (cm) | 5th- 2001 SA | 5.3 | 8.0 | 13.2 | M |
|  |  | 10th- 2001 SA | 4.9 | 4.6 | 6.0 | M |
|  |  | 15th- 2001 SA | 2.8 | 2.7 | 4.2 | M |
| 16 | Number of Carpels per Capsule | All | 2 | 2 | 2 |  |
| 17 | Capsule Length (cm) | 2000 UV | 2.9 | 2.7 | 2.2 | M |
|  |  | 2001 UV | 2.9 | 2.8 | 2.3 | M |
| 18 | Seed Weight per Capsule (g) | 2000 UV | 0.186 | 0.202 | 0.216 | M |
|  |  | 2001 UV | 0.198 | 0.213 | 0.252 | M |
| 19 | Capsule Weight per Capsule (g) | 2000 UV | 0.118 | 0.108 | 0.113 |  |
|  |  | 2001 UV | 0.157 | 0.138 | 0.169 |  |
| 20 | Capsule Weight per cm of Capsule (g) | 2000 UV | 0.041 | 0.040 | 0.055 | M |
|  |  | 2001 UV | 0.053 | 0.048 | 0.073 | M |
| 21 | Visual Shatter Resistance | All | W | W | W |  |
| 22 | Shaker Shatter Resistance (%) | 2000 UV | 77 | 79 | 72 |  |
|  |  | 2001 UV | 79 | 76 | 74 |  |
| 23 | Capsule Shattering Type | All | SR | SR | SR |  |
| 24 | Non-dehiscent Test | All | ND | ND | ND |  |
| 25 | Days to Flowering | 2000 UV | 39 | 37 | 41 | C |
|  |  | 2001 UV | 39 | 36 | 40 | C |
| 26 | Days to Flower Termination | 2000 UV | 78 | 75 | 79 | C |
|  |  | 2001 UV | 69 | 66 | 72 | C |
| 27 | Days to Physiological Maturity | 2000 UV | 91 | 87 | 96 | C |
|  |  | 2001 UV | 97 | 92 | 103 | C |
| 28 | Seed Color | All | BF | BF | BF |  |
| 29 | Seed Weight-100 Seeds from Whole Plant (g) | 2000 UV | 0.25 | 0.25 | 0.30 | C |
|  |  | 2001 UV | 0.27 | 0.27 | 0.31 | C |
| 30 | Uvalde Kill Resistance | 2000 UV | 4.60 | 5.67 | 5.60 | C |
|  |  | 2001 UV | 5.67 | 6.22 | 7.22 | C |
| 31 | Resistance to Fusarium Wilt (F. oxysporum) | 1998–2001 UV | 5 | 6 | 7 | C |
| 32 | Resistance to Phytophtora Stem Rot (P. parasitica) |  | NT | NT | NT |  |
| 33 | Resistance to Charcoal Rot (Macrophomina phaseoli) |  | NT | NT | NT |  |
| 34 | Resistance to Bacterial Black Rot (Pseudomonas sesami) | 1997 OK | NEC | NEC | NT |  |
| 35 | Resistance to Silverleaf White Fly (Bemisia argentifolii) | 2000 UV | NEC | NEC | NEC |  |
| 36 | Resistance to Green Peach Aphid (Myzus persica) | 2000 UV | NEC | NEC | NEC |  |
| 37 | Resistance to Pod Borer (Heliothis spp.) | 2001 UV | NEC | NEC | NEC |  |
| 38 | Resistance to Army Worms (Spodoptera spp.) |  | NT | NT | NT |  |
| 39 | Resistance to Cabbage Loopers (Pieris rapae) |  | NT | NT | NT |  |

[a] B = true branches; UV = Uvalde nursery; M = medium maturity class of 95–104 days; E = early maturity class of 85–94 days; B1M = phenotype of true branches, single capsules per leaf axil, and medium maturity class of 95–104 days; B1E = phenotype of true branches, single capsules per lead axil, and early maturity class of 85–94 days; SA = San Angelo nursery; W = weather visual seed retention >75%; SR = shatter resistant; ND = non-dehiscent; BF = buff color; NT = not tested; NEC = no economic damage-not enough disease to do ratings; and OK = Oklahoma nursery planted east of Clinton, Oklahoma (latitude 35°29' north, longitude 99°29' west, 489 m elev) in early to middle June from 1996–1997; mean rainfall is 667 mm annually with a mean of 281 mm during the growing season; average daily temperatures range from a low of 3° C. in January and an average high of 28° C. in July; the nursery planted on 91 cm beds; the nursery rainfed; the fertility 20 units of nitrogen.

The morphological differences show how S26 is different from S24 and S25, but these are not commercially significant. The three major areas of morphological differences are in the internode length, the size of the leaves, and the capsule characters.

S26 has a longer *Average Internode Length within Capsule Zone* than S24 and S25. This character does not generally have an effect on any commercially important characters.

S26 has longer leaves, wider leaves and longer petioles than S24 and S25 as shown in *Leaf Length, Leaf Blade Length, Leaf Blade Width*, and *Petiole Length*. The differences on the 10th leaf are not as significant. With the present agronomic practices, the sizes of the leaves have no commercial significance.

S26 has a shorter and wider capsule than S24 and S25 as shown in *Capsule Length* and *Capsule Weight per cm of Capsule*. As mentioned before, there is a slight positive correlation between capsule width and *Capsule Weight per cm of Capsule*. Wongyai (Wongyai W. and S. Juttpompong, 1992. "Indirect selection for seed weight in sesame using capsule size as a criteria," *Sesame and Safflower Newsletter*, No. 7, p.4–7) showed a positive correlation between capsule width and *Seed Weight—100 Seeds from Whole Plant* which is a commercially significant difference as discussed below. There is also a slight positive correlation between seed weight and *Seed Weight per Capsule* with S26 having a higher weight per capsule than S24 and S25. Despite these slight positive correlations, capsule width is not used as a commercially significant selection filter, e.g., there are commercially viable lines with narrow capsules.

The major commercial differences between S26 and the S24 and S25 are in the maturity, the yields as affected by resistance to disease and to drought, and seed weight.

*Maturity Class, Plant Phenotype, Days to Flowering, Days to Flower Termination,* and *Days to Physiological Maturity* are all related. *Maturity Class* and *Plant Phenotype* are based on *Days of Physiological Maturity*, and there is a high positive correlation between *Days to Physiological Maturity* and *Days to Flowering* and *Days to Flower Termination*. Basically, the later the start and end of flowering, the longer it takes to reach physiological maturity. S26 is later than S24 and S25 restricting the geographical range of S26 to central Oklahoma and south.

*Yield at Drydown* in Uvalde, *Uvalde Kill Resistance*, and *Resistance to Fusarium Wilt* are all related. The yields in Uvalde of S26 were greater than S24 and S25. The yields of S24 were reduced by greater susceptibility to root rots than S25 and S26. In years when there is little disease, the *Yield at Drydown* in Uvalde of S24, S25, and S26 are not statistically different.

*Yield at Drydown* in San Angelo and *Resistance to Drought* are related. S26 is more drought resistant than S24 which is more drought resistant than S25. In 2000 in San Angelo, there was a drought with very low moisture in the soil profile at planting, and the one irrigation of less than 50 mm was applied too late to help the crop. S26 outyielded S24 by 93% and S25 by 348%. In a normal year such as 2001, S26 outyielded S24 by 6% and S25 by 11%. S24 and S25 are not recommended for rainfed conditions where there is low annual rainfall or where there is a drought in progress. S26 is the choice variety under these conditions.

On May 10, 2002, a deposit of at least 2500 seeds of sesame plant S26 was made by Sesaco Corporation under the provisions of the Budapest Treaty with the American Type Culture Collection (ATCC), 10801 University Boulevard, Manassas, Va. 20110-2209, and the deposit was given ATCC Patent Deposit Designation No. PTA-4317. This deposit will be maintained in the ATCC depository for a period of 30 years or 5 years after the last request or for the enforceable life of the patent, whichever is longer. Should the seeds from the sesame line S26 deposited with the American Type Culture Collection become inviable, the deposit will be replaced by Sesaco Corporation upon request.

The foregoing invention has been described in some detail by way of illustration and characters for purposes of clarity and understanding. However, it will be obvious that certain changes and modifications may be practiced within the scope of the invention as limited only by the scope of the appended claims.

I claim:

1. Seed of sesame variety designated S26, a sample of said seed having been deposited under ATCC Accession No. PTA-4317.

2. A sesame plant or part thereof produced by growing the seed of sesame variety S26, a sample of said seed having been deposited under ATCC Accession No. PTA-4317.

3. Pollen of said sesame plant of claim 2.

4. A sesame plant having all the physiological and morphological characteristics of sesame variety S26, a sample of the seed of said variety having been deposited under ATCC Accession No. PTA-4317.

5. A sesame plant having all the physiological and morphological characteristics of a sesame plant produced by growing seed sesame variety S26, a sample of said seed having been deposited under ATCC Accession No. PTA-4317.

6. A tissue culture of regenerable cells produced from seed of sesame variety S26, sample of said seed having been deposited under ATCC Accession No. PTA-4317.

7. A tissue culture of regenerable cells produced from sesame plant S26 or a part thereof produced by growing the seed of sesame variety S26, a sample of said seed having been deposited under ATCC Accession No. PTA-4317.

8. A sesame plant regenerated from a tissue culture of regenerable cells produced from seed of sesame variety S26, a sample of said seed having been deposited under ATCC Accession No. PTA-4317, wherein said regenerated sesame plant has all the physiological and morphological characteristics of said sesame variety S26.

9. A sesame plant regenerated from a tissue culture of regenerable cells produced from a sesame plant produced by growing the seed of sesame variety S26, a sample of said seed having been deposited under ATCC Accession No. PTA-4317, wherein said regenerated sesame plant has all the physiological and morphological characteristics of said sesame variety S26.

10. A method of producing sesame seed, comprising crossing a first parent sesame plant with a second parent sesame plant and harvesting the resultant sesame seed, wherein said first or second parent sesame plant was produced by growing seed of sesame variety S26, a sample of said seed having been deposited under ATCC Accession No. PTA-4317.

* * * * *

UNITED STATES PATENT AND TRADEMARK OFFICE
CERTIFICATE OF CORRECTION

PATENT NO. : 6,781,031 B2
DATED : August 24, 2004
INVENTOR(S) : Derald Ray Langham It is certified that error appears in the above-identified patent and that said Letters Patent is hereby corrected as shown below:

Title page,
Item [73], Assignee, replace "(FR)" with -- TX --.

Column 5,
Line 39, replace "(SO4)" with -- (S04) --.
Line 55, replace "(SO2)" with -- (S02) --.

Column 7,
Line 49, replace "(SO6)" with -- (S06) --.

Column 8,
Line 10, replace ("SO5)" with -- (S05) --.

Column 36,
Line 36, replace "S02 through SO," with -- S02 through S10, --.
Line 46, replace "S1" with -- S11 --.
Line 55, replace "Fusarium, Phytophtora, and Macrophomina" with
-- *Fusarium, Phytophtora,* and *Macrophomina* --.

Column 37,
Line 51, replace "SO4" with -- S04 --.

Column 44,
Line 18, replace "seed sesame" with -- seed of sesame --.

Signed and Sealed this

Eighth Day of February, 2005

JON W. DUDAS
*Director of the United States Patent and Trademark Office*